(12) United States Patent
Favet et al.

(10) Patent No.: US 7,979,122 B2
(45) Date of Patent: Jul. 12, 2011

(54) IMPLANTABLE SUDDEN CARDIAC DEATH PREVENTION DEVICE WITH REDUCED PROGRAMMABLE FEATURE SET

(75) Inventors: Mike Favet, San Jose, CA (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1725 days.

(21) Appl. No.: 10/821,125

(22) Filed: Apr. 8, 2004

(65) Prior Publication Data

US 2004/0215239 A1 Oct. 28, 2004

Related U.S. Application Data

(60) Provisional application No. 60/462,272, filed on Apr. 11, 2003.

(51) Int. Cl.
*A61N 1/362* (2006.01)
(52) U.S. Cl. ............... 607/4; 607/9; 607/11; 607/14
(58) Field of Classification Search ............... 607/4, 9, 607/11, 14
See application file for complete search history.

(56) References Cited

U.S. PATENT DOCUMENTS

| | | | |
|---|---|---|---|
| 4,312,355 A | 1/1982 | Funke | |
| 4,562,841 A | 1/1986 | Brockway et al. | |
| 4,693,253 A | 9/1987 | Adams | |
| 4,784,162 A | 11/1988 | Ricks et al. | |
| 4,827,943 A | 5/1989 | Bornn et al. | |
| 4,940,054 A | 7/1990 | Grevis et al. | |
| 4,953,551 A | 9/1990 | Mehra et al. | |
| 5,003,975 A | 4/1991 | Hafelfinger et al. | |
| 5,036,849 A | 8/1991 | Hauck et al. | |
| 5,074,301 A * | 12/1991 | Gill | 607/4 |
| 5,133,353 A | 7/1992 | Hauser | |
| 5,156,157 A | 10/1992 | Valenta, Jr. et al. | |
| 5,170,784 A | 12/1992 | Ramon et al. | |
| 5,179,945 A | 1/1993 | Van Hofwegen et al. | |
| 5,188,106 A | 2/1993 | Nappholz et al. | |
| 5,203,348 A | 4/1993 | Dahl et al. | |
| 5,209,229 A | 5/1993 | Gilli | |

(Continued)

FOREIGN PATENT DOCUMENTS

EP     1234597     8/2002

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner* — Carl H Layno
*Assistant Examiner* — Deborah Malamud
(74) *Attorney, Agent, or Firm* — Hollingsworth & Funk, LLC

(57) ABSTRACT

Preventing sudden cardiac death involves providing an implantable device configured to deliver only two forms of cardiac therapy, the two forms of cardiac therapy including an anti-tachyarrhythmia therapy and an asystole prevention pacing therapy. The tachyarrhythmia therapy is delivered in response to detecting a tachyarrhythmia, and the pacing therapy is delivered in response to detection of cardiac asystole. An implantable cardiac device for preventing sudden cardiac death may be configured to be fully operational upon setting a therapy On/Off parameter and two or less programmable parameters associated with therapy delivery. Control circuitry configures the device for operation to prevent sudden cardiac death after programming the two or less programmable parameters and enabling the therapy On/Off parameter.

20 Claims, 16 Drawing Sheets

U.S. PATENT DOCUMENTS

| | | |
|---|---|---|
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,306,293 A | 4/1994 | Zacouto |
| 5,313,953 A | 5/1994 | Yomtov et al. |
| 5,314,430 A | 5/1994 | Bardy |
| 5,314,459 A | 5/1994 | Swanson et al. |
| 5,318,593 A | 6/1994 | Duggan |
| 5,318,594 A | 6/1994 | Limousin et al. |
| 5,318,597 A | 6/1994 | Hauck et al. |
| 5,331,966 A | 7/1994 | Bennett et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,187 A | 2/1995 | Freeman |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,717 A | 5/1995 | Salo et al. |
| 5,439,482 A | 8/1995 | Adams et al. |
| 5,441,518 A | 8/1995 | Adams et al. |
| 5,468,254 A | 11/1995 | Hahn et al. |
| 5,527,345 A | 6/1996 | Infinger |
| 5,531,779 A | 7/1996 | Dahl et al. |
| 5,545,202 A | 8/1996 | Dahl et al. |
| 5,601,607 A | 2/1997 | Adams |
| 5,603,331 A | 2/1997 | Heemels et al. |
| 5,603,732 A | 2/1997 | Dahl et al. |
| 5,606,969 A | 3/1997 | Butler et al. |
| 5,607,385 A | 3/1997 | Francischelli et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,782,883 A | 7/1998 | Kroll et al. |
| 5,797,967 A | 8/1998 | KenKnight |
| 5,814,079 A | 9/1998 | Kieval |
| 5,827,326 A | 10/1998 | Kroll et al. |
| 5,869,970 A | 2/1999 | Sanchez-Zambrano |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,044,298 A | 3/2000 | Salo et al. |
| 6,050,940 A | 4/2000 | Braun et al. |
| 6,055,454 A | 4/2000 | Heemels |
| 6,148,230 A | 11/2000 | KenKnight |
| 6,205,357 B1 | 3/2001 | Ideker et al. |
| 6,221,011 B1 | 4/2001 | Bardy |
| 6,270,475 B1 | 8/2001 | Bestetti et al. |
| 6,277,072 B1 | 8/2001 | Bardy |
| 6,280,380 B1 | 8/2001 | Bardy |
| 6,280,462 B1 | 8/2001 | Hauser et al. |
| 6,303,270 B1 | 10/2001 | Flaim et al. |
| 6,304,773 B1 | 10/2001 | Taylor |
| 6,306,088 B1 | 10/2001 | Krausman |
| 6,312,378 B1 | 11/2001 | Bardy |
| 6,314,319 B1 | 11/2001 | Kroll et al. |
| 6,336,903 B1 | 1/2002 | Bardy |
| 6,351,670 B1 | 2/2002 | Kroll |
| 6,358,203 B2 | 3/2002 | Bardy |
| 6,368,284 B1 | 4/2002 | Bardy |
| 6,375,614 B1 | 4/2002 | Braun et al. |
| 6,398,728 B1 | 6/2002 | Bardy |
| 6,409,675 B1 | 6/2002 | Turcott |
| 6,415,174 B1 | 7/2002 | Bebehani et al. |
| 6,438,410 B2 | 8/2002 | Hsu et al. |
| 6,440,066 B1 | 8/2002 | Bardy |
| 6,442,433 B1 | 8/2002 | Linberg |
| 6,450,957 B1 | 9/2002 | Yoshimi |
| 6,454,708 B1 | 9/2002 | Ferguson et al. |
| 6,480,733 B1 | 11/2002 | Turcott |
| 6,491,639 B1 | 12/2002 | Turcott |
| 6,512,940 B1 | 1/2003 | Brabec et al. |
| 6,522,915 B1 | 2/2003 | Ceballos et al. |
| 6,556,862 B2 | 4/2003 | KenKnight et al. |
| 6,564,106 B2 | 5/2003 | Guck et al. |
| 6,607,509 B2 | 8/2003 | Bobroff et al. |
| 6,615,083 B2 | 9/2003 | Kupper |
| 6,618,618 B2 | 9/2003 | Kalgren et al. |
| 6,622,046 B2 | 9/2003 | Fraley et al. |
| 6,625,491 B2 | 9/2003 | Ripart |
| 6,628,986 B1 | 9/2003 | Mouchawar et al. |
| 6,704,590 B2 | 3/2004 | Haldeman |
| 6,708,058 B2 | 3/2004 | Kim et al. |
| 6,799,072 B2 | 9/2004 | Ries et al. |
| 6,845,268 B2 | 1/2005 | Hill et al. |
| 6,892,095 B2 | 5/2005 | Salo |
| 6,895,273 B2 | 5/2005 | Seim et al. |
| 6,922,589 B2 | 7/2005 | Stahmann et al. |
| 7,189,204 B2 | 3/2007 | Ni et al. |
| 7,252,640 B2 | 8/2007 | Ni et al. |
| 7,289,854 B2 | 10/2007 | Bardy et al. |
| 7,346,392 B2 | 3/2008 | KenKnight |
| 7,369,333 B2 | 5/2008 | Stahmann et al. |
| 7,392,081 B2 | 6/2008 | Wagner et al. |
| 7,515,969 B2 | 4/2009 | Tockman et al. |
| 7,570,997 B2 | 8/2009 | Lovett et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |
| 2004/0215240 A1 | 10/2004 | Lovett et al. |
| 2004/0230229 A1 | 11/2004 | Lovett et al. |
| 2004/0230230 A1 | 11/2004 | Lindstrom |
| 2005/0004615 A1 | 1/2005 | Sanders |

FOREIGN PATENT DOCUMENTS

| EP | 1304137 | 4/2003 |
|---|---|---|
| WO | WO 92/20402 | 11/1992 |
| WO | WO0009206 | 2/2000 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. on Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33. pp. 243-247 (Feb. 1974).

John C. Schuder et al., *Experimental Ventricular Defibrillation with an Automatic and Completely Implanted System*, Trans. Am. Soc. Artif. Int. Organs, vol. 16. pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Lang et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al.. *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

Press Release Biotronik 2003. *BIOTRONIK Announces FDA Approval of the Low-Cost Cardiac Airbag™ Implantable Cardioverter Defibrillator System*. Portland, Oregon. cardiac-airbag@biotronikusa.com. 2 pages (May 15, 2003).

BIOTRONIK © 2003 Website product literature. *Cardiac Airbag™/Meeting the Needs of the At Risk Patient*. 3 pages.

Altamura et al., Emergency Cardiac Pacing for Severe Bradycardia, Pace, vol. 13, Dec. 1990, 6 pages.

www.medtronic.com/reveal/new.html, Medtronic, Inc. 2001. New Diagnostic Tool—Reveal® Insertable Loop Recorder. Medtronic Website, updated Jul. 12, 2001 (3 sheets). Printed from the internet Sep. 16, 2008.

Satoh et al., Role of hypoxic drive in regulation of postapneic ventilation during sleep in patients with obstructive sleep apnea, First Department of Internal Medicine, Tohoku University School of Medicine, Sendai, Japan, Mar. 1991, abstract only.

File Wrapper for U.S. Appl. No. 10/820,642 as retrieved from U.S. Patent Office system on Oct. 20, 2010, 184 pages.

* cited by examiner

Shock          Pacing at 70 ppm

IMPLANTABLE SUDDEN CARDIAC DEATH PREVENTION DEVICE WITH REDUCED PROGRAMMABLE FEATURE SET

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to cardiac systems and methods that prevent sudden cardiac death.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachyarrythmia. Tachyarrythmia may have its origin in either the atria or the ventricles. Tachyarrythmias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachyarrythmia occurs, for example, when electrical activity arises in the ventricular myocardium at a rate more rapid than the normal sinus rhythm. Ventricular tachyarrythmia includes ventricular tachycardia and ventricular fibrillation. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

SUMMARY OF THE INVENTION

The present invention is directed to implantable devices and methods for preventing sudden cardiac death. According to one embodiment, an implantable cardiac device includes a housing configured for implantation in a patient. Energy delivery circuitry is provided in the housing and configured to deliver only two forms of cardiac therapy. The two forms of cardiac therapy include a non-physiologic, life sustaining pacing therapy and a therapy to treat a tachyarrhythmia. The pacing therapy is preferably a therapy deliverable at a rate lower than a bradycardia pacing rate. Detection circuitry is provided in the housing and configured to detect cardiac rhythms. A lead system is coupled to the energy delivery and detection circuitry and includes one or more lead electrodes. Control circuitry is provided in the housing and coupled to the energy delivery circuitry and the detection circuitry. The control circuitry is configured to coordinate delivery of the tachyarrhythmia therapy in response to detection of a tachyarrhythmia requiring treatment and delivery of the non-physiologic, life sustaining pacing therapy in response to detection of cardiac asystole.

According to another embodiment, a method of preventing sudden cardiac death involves providing an implantable device configured to deliver only two forms of cardiac therapy, wherein the two forms of cardiac therapy include a therapy to treat a tachyarrhythmia and an asystole prevention pacing therapy. The method also involves detecting a cardiac condition necessitating cardiac therapy. The method further involves delivering the tachyarrhythmia therapy in response to detecting a tachyarrhythmia requiring treatment, and delivering the pacing therapy in response to detection of cardiac asystole.

In accordance with another embodiment, an implantable cardiac device for preventing sudden cardiac death includes a housing configured for implantation in a patient. Energy delivery circuitry is provided in the housing and configured to deliver a therapy to treat a tachyarrhythmia and a pacing therapy deliverable at a rate lower than a bradycardia pacing rate. Detection circuitry is provided in the housing and configured to detect cardiac rhythms. A lead system is coupled to the energy delivery and detection circuitry, and includes one or more lead electrodes. The device further includes a memory configured to store a therapy On/Off parameter and two or less programmable parameters associated with therapy delivery. Control circuitry is provided in the housing and coupled to the memory, energy delivery circuitry, and detection circuitry. The control circuitry configures the device for operation to prevent sudden cardiac death after programming the two or less programmable parameters and enabling the therapy On/Off parameter.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
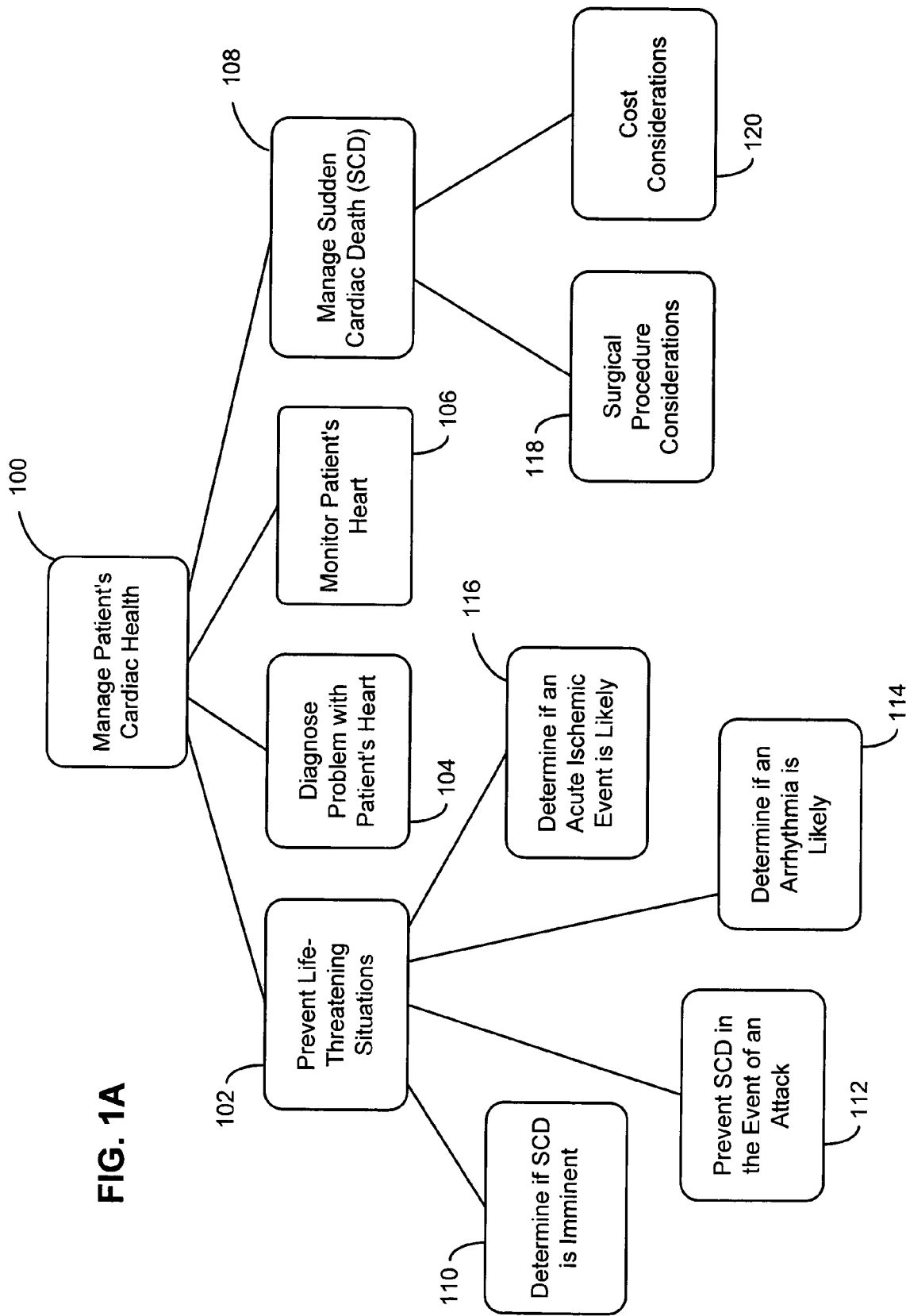
FIG. 1A is a diagram depicting various aspects concerning the management of a patient's cardiac health as facilitated by use of a sudden cardiac death prevention (SCDP) device of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

An implantable cardiac device of the present invention finds particular utility in the context of preventing sudden cardiac death (SCD) in patients that may not require a traditional implantable cardiac defibrillator (ICD). Although ICDs are very effective at preventing SCD, most people at risk of SCD are not provided with implantable defibrillators. Many people that are at risk of SCD, for example, may not have a history of arrhythmias or other comorbidities that are often considered threshold factors that must be present before a person can receive an ICD. The high costs of conventional ICDs (device and surgical implant costs), and the relatively stringent requirements that a candidate patient must satisfy in order to justify the risks and costs of conventional ICD implantation, may also significantly limit the number of patients that can receive a conventional ICD. Other reasons why people at risk of SCD do not receive conventional ICDs, particularly those that have a cardiac pacing capability, include the limited number of physicians qualified to perform lead/electrode implantation and pacing threshold determinations, and a limited number of surgical facilities adequately equipped to accommodate such cardiac device implant procedures. Each year, SCD claims the lives of some 300,000 Americans—with 80% to 90% of those deaths caused by ventricular fibrillation.

It is believed that an implantable cardiac device of the present invention may be appropriate for implantation in a significantly larger patient population than that for which conventional ICDs are appropriate. It is also believed that a larger physician population is available for implanting a cardiac device of the present invention than is available for conventional ICD implantation. It is further believed that these factors in addition to a significant reduction in device and surgical delivery costs allows for the prevention of sudden cardiac death in a significant percentage of the population that may otherwise not receive the life saving benefits offered by conventional ICDs.

These and other advantages associated with the present invention may be realized in an implantable sudden cardiac death prevention device (SCDP device), various embodiments of which are described below. In contrast to conventional ICDs that provide a vast array of diagnostic and therapeutic features, including dozens or hundreds of programmable parameters, an SCDP device of the present invention is implemented with relatively few features and programmable parameters. By way of example, an embodiment of an SCDP device of the present invention has two programmable parameters that effect therapy delivery and a therapy On/Off toggle that, once selected, allow the SCDP device to become fully operative for preventing sudden cardiac death in a patient. The two programmable parameters, according to embodiments of the present invention, are a sensing floor adjustment parameter and a rate threshold for therapy parameter. The therapy On/Off toggle, which may be considered a third programmable parameter, enables and disables SCDP device therapy.

By way of further example, an embodiment of an SCDP device of the present invention provides only two forms of cardiac therapy, neither of which requires that pacing threshold determinations be made at the time of implant or thereafter, nor the need to position cardiac leads/electrodes in the heart with great precision. The two forms of cardiac therapy, according to embodiments of the present invention, are tachyarrhythmia therapy and asystole prevention therapy. An SCDP device of the present invention, for example, is preferably usable by a physician not expert in arrhythmia management.

Pacing threshold testing can be a challenge during implant and there is complexity associated with performing the threshold test. Pacing threshold tests can motivate intraoperative lead revisions that require skill and take time. Since pacing thresholds are not a major concern when using an SCDP device of the present invention, none of the factors will be an issue. Eliminating pacing threshold determinations and precise electrode delivery requirements provides the opportunity for a broader population of cardiologists and general surgeons to implant an SCDP device of the present invention in a broader range of candidate patients.

In accordance with embodiments of the present invention, an SCDP device provides basic functionality via a reduced feature set needed to treat life-threatening ventricular arrhythmias (LTVAs). LTVAs of particular interest include ventricular fibrillation and polymorphic ventricular tachycardia, but typically exclude non-sustained monomorphic ventricular tachycardia and electromechanical disassociation (EMD). Certain SCDP device embodiments of the present invention preferably treat LTVAs and cardiac asystole only, and are fully operational upon selection of rate threshold for therapy, sensing floor adjustment, and therapy On/Off parameters.

An SCDP device of the present invention is preferably easy to integrate into a physician's practice. Typically, no routine follow-up should be required. A minimal set of automatic diagnostics are preferably implemented and used to indicate that physician follow-up should occur. This set of automatic diagnostics preferably include indications concerning low battery, noise leading to diverted therapy, electrode fault, pulse generator fault, and event/therapy detected/delivered.

It is desirable that an SCDP device of the present invention prevent sudden cardiac death as well as conventional ICDs. For example, all-cause mortality Kaplan-Meier curves for an SCDP device and conventional ICDs are preferably statistically indistinguishable. An SCDP device may, for example, demonstrate an LTVA conversion rate of ≧97.3% within 1 minute of arrhythmia onset. In addition, it is desirable that an SCDP device deliver few inappropriate therapies, and that device specificity approach 100%. One approach by which specificity may be increased involves increasing the time taken by the SCDP device to perform arrhythmia detection and confirm the presence of an LTVA.

An SCDP device of the present invention makes device implant easier and simpler relative to conventional ICD implantation. According to one lead delivery approach, a Swan-Ganz type catheter includes a distal inflation balloon that is carried within an access vein by natural blood flow to the right atrium. The catheter may include a pressure sensor arrangement that is used to properly locate the lead/electrode, thereby obviating the need for fluoroscopy. Once in position, the lead is slid over the catheter and advanced to an implant site in the right ventricle. The lead typically includes a tip electrode and a tine that is used to implant the lead in myocardial tissue within the right ventricle. Because traditional pacing (e.g., bradycardia pacing) is not performed by an SCDP device of the present invention, which eliminates pacing threshold optimization concerns, precision placement of the lead/electrode is typically not critical.

According to one approach for implanting the SCDP device housing, the device housing may be implanted by use of a maximum of two incisions less than about 5 inches long and less than about 2 inches deep. Only one layer of suture is typically needed to close. SCDP device components, for example, need only occupy a portion of approximately one quadrant of the chest as viewed cross-sectionally. The maximum distance between SCDP device components may be about 6 inches, for example. The procedure design, tools, and physician skill combine for a short, predictable, and efficient operation to implant an SCDP device and lead of the present invention.

Further, an SCDP device of the present invention is relatively comfortable for the patient, and is relatively small. For example, the housing of the SCDP device is preferably placed in the thoracic portion of the torso, preferably ventrally. According to various embodiments, for example, the maximum size of the SCDP housing is preferably 60 cc, and stores a maximum of about 70 joules. According to one non-limiting, illustrative embodiment, the maximum device weight, thickness, and footprint may be about 300 g, about 25 mm, and about 16,000 $mm^2$, respectively.

An SCDP device of the present invention advantageously enables an "implant and forget" paradigm. The number of complications associated with SCDP device use is less than that associated with conventional ICD use. Such complications include, for example, device reliability issues, electrode migration, infection, pain, and erosion.

Consistent with this paradigm is the process of implanting an SCDP device of the present invention under an "inductionless" paradigm. With sufficient clinical data, SCDP devices may be designed to deliver sufficiently high defibrillation energies that are highly likely to terminate cardiac fibrillation for a broad population of patients. In this scenario, SCDP device patients need not be subjected to ventricular fibrillation/shock testing at the time of SCDP device implant. In the context of an implant procedure where ventricular fibrillation/shock testing is required or desired, a "one-button" approach to conducting ventricular fibrillation/shock testing may be employed, such as by activation of a VF/shock test button provided on a hand-held, portable interface device of the type described previously with regard to FIG. 1B. Upon activation of the VF/shock test button, for example, the portable interface device initiates delivery of ventricular fibrillation induction energy and subsequently converts an induced arrhythmia to assure the implanting physician that the SCDP device functions properly.

As was discussed briefly above, an SCDP device implemented in accordance with the present invention presents less cost to the health care system than does a conventional ICD, and requires only minimal support. For example, the implant procedure should be both shorter in duration and less complicated than that of a conventional ICD, which should result in reduced costs to the healthcare system. Further, facility requirements for SCDP device implant are less sophisticated and therefore less expensive than required for conventional ICDs. Moreover, a physician or caregiver with less-specialized training than an electrophysiologist can perform the simplified implant procedure, resulting in reduced associated expenses.

An SCDP device of the present invention may be constructed using relatively inexpensive components. Using less expensive components in the construction of an SCDP relative to those used in conventional ICDs can further reduce costs to the healthcare system. A tradeoff involved in component selection is generally a larger volume of component (and device), due to use of previous-generation (i.e., less miniaturized and refined) components.

The following cost reductions to the health care system can be realized by use of an SCDP device of the present invention: elimination of follow-up appointments, minimal programming, automatic diagnostics, reduced device manufacturing costs, implantation times of 30 minutes or less ("skin-to-skin") using a less sophisticated surgical site, elimination of fluoroscopy, and reduction in anesthesia requirements relative to costs associated with conventional ICD use.

In certain embodiments, an SCDP device of the present invention may be implemented to address needs of the physician and patient other than prevention of sudden cardiac death. An SCDP device of the present invention may incorporate additional features, yet retain many of the advantages and attributes described above. Such additional features include ischemia detection, coronary artery disease detection, a Holter monitor equivalent capability, and a stress test equivalent capability.

Turning now to Figures, FIG. 1A is a diagram depicting various aspects concerning the management 100 of a patient's cardiac health as facilitated by use of an SCDP device of the present invention. The aspects indicated in FIG. 1 are representative of functions, objectives or outcomes that can be achieved using an SCDP device of the present invention, and are provided for non-limiting, illustrative purposes only. As was previously described, an SCDP device of the present invention is preferably implemented with a reduced feature set and limited number of programmable parameters, yet provide for a number of important capabilities appropriate for a broad population of patients that are at risk of sudden cardiac death. An SCDP device of the present invention may, for example, be implemented to prevent life-threatening situations 102, diagnose problems with a patient's heart 104, monitor a patient's heart 106, and/or manage cardiac sudden death 108.

Concerning prevention of life-threatening situations 102, an SCDP device of the present invention may be implemented to determine if SCD is imminent 110 and prevent SCD in the event of an attack 112. In some embodiments, an SCDP device may be implemented to determine if an arrhythmia is likely 114 and/or determine if an acute ischemic event is likely 116. For example, information acquired by an SCDP device may be used to predict the likelihood of a future arrhythmia or acute ischemic event. Such prediction information may subsequently be evaluated by a physician/caregiver.

The patient's heart may be monitored 106 for a number of purposes, including determining whether the SCDP device is properly addressing the patient's cardiac condition, such as by determining the adequacy of current treatment. For example, monitoring data may be used to confirm that the SCDP device is properly treating adverse cardiac events for a particular patient. Monitoring data may also be used to determine whether the patient's cardiac condition has negatively progressed beyond the treatment capabilities of the SCDP device. In such a case, the monitoring data may be used to determine which type of cardiac device and functionality (e.g., conventional ICD or ICD with resynchronization pacing) is appropriate given a negative change in the patient's cardiac health.

Monitoring a patient's cardiac activity using an SCDP device may also assist the physician in determining patient compliance with a medication regimen. For example, monitoring data acquired by the SCDP device may demonstrate whether or not a patient is taking an anti-arrhythmia medication or other medication that effects cardiac activity. SCDP device monitoring data may also be used to determine if a patient runs the risk of prescription drug toxicity, for example.

An SCDP device is useful when diagnosing a problem 104 with a patient's cardiac health 104, particularly in cases where the problem is difficult to identify. For example, an SCDP device may be used to determine whether or not a patient's symptom is cardiac-related. An SCDP device may also be used to determine if a serious arrhythmia is present, or if the patient has suffered an episode or attack. An SCDP device may further be used to determine what factors or events pre-disposed the patient to an episode or attack. Moreover, an SCDP device may be used to determine if the patient's cardiac condition has progressed into heart failure.

An SCDP device of the present invention may enhance a physician's ability to manage 108 various aspects of sudden cardiac death impacting those patient under the care of the physician. From an operational perspective, various objectives concerning surgical procedures may be achieved by implanting an SCDP device of the present invention is comparison to conventional ICDs, for example. Such achievable objectives include minimizing the size and depth of required incisions, minimizing the amount of tissue subject to dissection, minimizing the amount of bleeding, minimizing the risk of infection during the procedure, and minimizing the risk of allergic reaction in the patient.

From a cost prospective, as was discussed briefly above, an SCDP device of the present invention can be implemented to successfully and significantly reduce costs 120 to the health care system associated with managing patient cardiac health. Because an SCDP device can be implemented so as to require little to no routine physician follow-up, the costs associated with repeated office visits and patient no-shows is reduced or eliminated. Unproductive physician/caregiver downtime, such as physician time required to travel to the procedure clinic or room, is minimized. The investment of capital equipment and infrastructure required to perform and support the implant procedure is minimized. Risks of product liability can be minimized. Profits for the office or clinic may also be increased. These and other advantageous capabilities and objectives may be realized through use of an SCDP device of the present invention as a central tool for managing patient cardiac health.

Figure 1B:
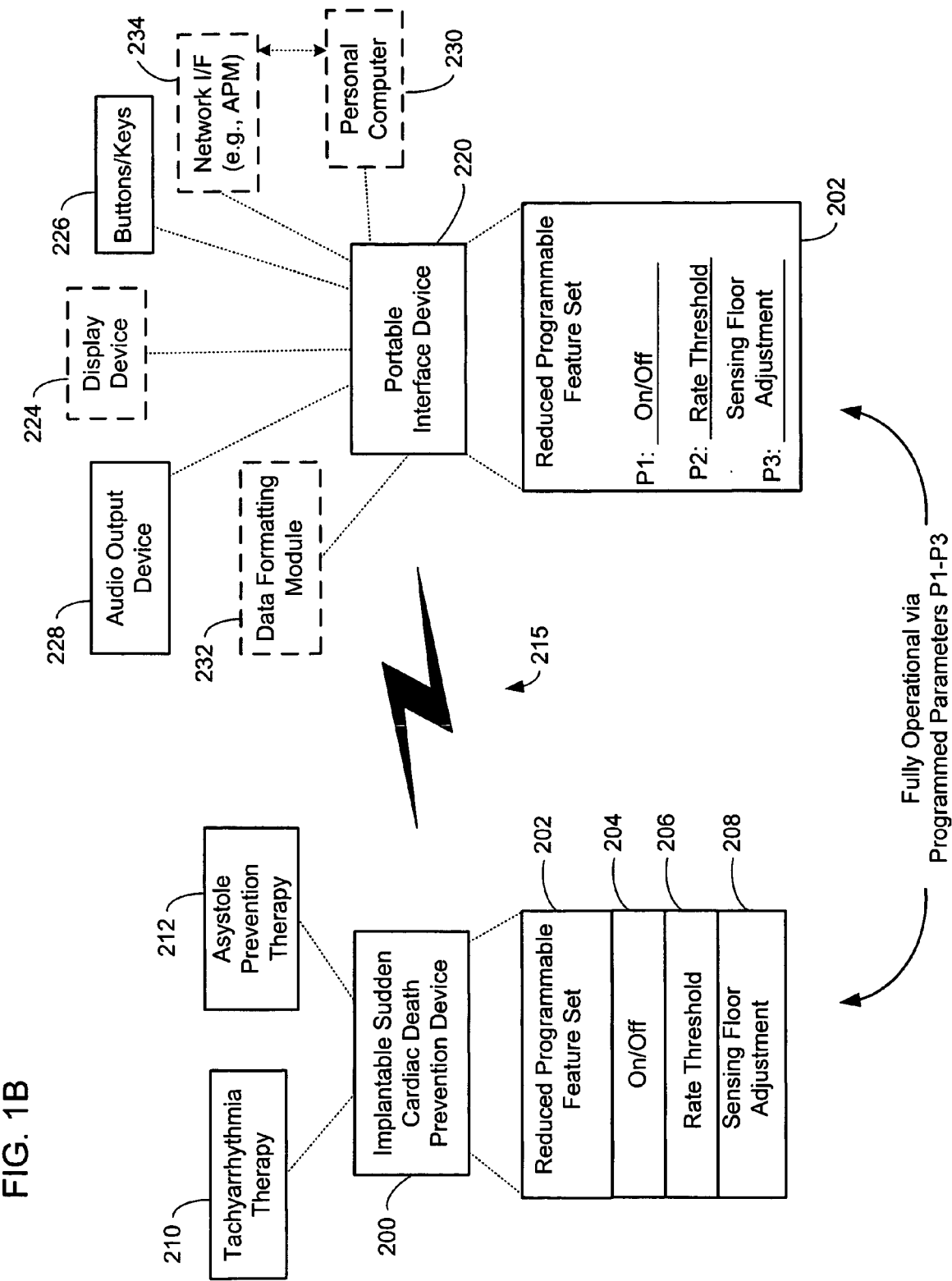
FIG. 1B is a block diagram of an SCDP device and system in accordance with embodiments of the present invention.

Referring now to FIG. 1B, there is shown a block diagram of an SCDP device and system in accordance with embodiments of the present invention. FIG. 1B shows an SCDP device 200 that includes a reduced programmable feature set 202. The reduced programmable feature set 202 according to this embodiment limits the capabilities of the SCDP device 200 to only those needed to treat sudden cardiac death with minimal programming, thereby increasing the number of candidate patients and physicians that can benefit from use of the device 200. In contrast to conventional ICDs having numerous therapeutic features that are enabled and/or modifiable by programming of upwards to 100 or more programmable parameters, an SCDP device 200 according to the embodiment depicted in FIG. 1B provides for only two forms of cardiac therapy and two programmable parameters, in addition to a therapy On/Off parameter. As shown in FIG. 1B, the SCDP device 200 is implemented to provide tachyarrhythmia therapy 210 and asystole prevention therapy 212. The SCDP device 200 can be fully programmed for operation by programming a rate threshold setting 206 and a sensing floor adjustment setting 208, and then turning on therapy by toggling a On/Off therapy setting 204.

Notwithstanding the limited number of features and programmable parameters implicated in the SCDP device embodiment of FIG. 1B, the SCDP device 200 can be enabled for full SCD prevention operation upon programming of the two programmable parameters 206, 208. Those skilled in the art will readily appreciate that enabling conventional ICDs for operation in a given patient is a time consuming procedure requiring the presence of a highly skilled physician, and typically a representative of the device manufacturer, to facilitate programming of the device for a particular patient. Those skilled in the art will also readily appreciate that conventional ICDs can be enabled for operation in a given patient only after programming dozens of programmable parameters through use of a relatively sophisticated and expensive programmer. By way of example, a specialized cardiologist would have to program dozens of parameters and disable numerous features of a conventional ICD in order to provide the reduced set of capabilities made immediately available by programming only two therapy parameters 206, 208 of the SCDP device 200 and turning the device ON 204, which may be performed by a general, rather than specialized, cardiologist.

The rate threshold parameter 206 refers to sensed ventricular rate. For example, the rate threshold 206 may be set to values within a range of about 150 to 250 beats per minute by the physician. The sensing floor adjustment parameter 208 refers to the minimum voltage amplitude required for the detection of a ventricular event. The sensing floor adjustment parameter 208 associated with intrathoracic (e.g., transvenous) implementations may be set to values within a range of about 0.05 mV to about 5 mV by the physician. The sensing floor adjustment parameter 208 associated with transthoracic (e.g., subcutaneous non-intrathoracic) implementations may be set to values within a range of about 0.25 mV to about 25 mV by the physician.

FIG. 1B also shows an interface device 220 that is configured to communicate with the SCDP device 200 via a wireless (e.g., RF) link 215. The interface device 220 is preferably configured for portability, preferably hand-held portability. The interface device 220 includes an input device arrangement, such as buttons and/or keys 226, that facilitate physician input or selection of a reduced set of programmable parameters.

The number of programmable parameters is typically less than about 10, more preferably five or fewer, and most preferably two or fewer. In various embodiments, and by way of example, the following programmable parameters may be used in addition to, or in place of, the rate threshold setting 206 and sensing floor adjustment setting 208:

A Morphology Discrimination Similarity Metric, such as a matching percentage for a single channel morphology based rhythm analysis algorithm or a feature correlation coefficient threshold for a two channel (rate and shock) morphological rhythm identification algorithm.

A Time-to-Classification parameter indicative of a duration between initial detection and time at which the SCDP device makes a determination as to whether or not therapy is indicated, where the therapy indication may be initial and may later be changed.

An Asystole Prevention Control, such as a rate or rhythm profile (such as increasing or decreasing rate).

An Enable ATP parameter.

An Enable Cardioversion parameter.

A Therapy "Aggressiveness" Control (e.g., aggressive, nominal, conservative), that loads a set of parameters pertaining to therapy and arrhythmia detection, such as rate, correlation match, shock strength, etc. The Aggressiveness control may enable serial delivery of an ATP and/or cardioversion therapy prior to or during a defibrillation therapy, such as during charging of defibrillation capacitors. For example, ATP therapy may first be delivered and, if unsuccessful, cardioversion therapy may then be delivered.

In one embodiment, the number of programmable or adjustable parameters is zero, assuming that a therapy On/Off parameter 204 is made available. In this embodiment, the rate threshold and sensing floor adjustment parameters 206, 208 are pre-established, non-programmable parameters. The values of the rate threshold and sensing floor adjustment parameters 206, 208 may be pre-established based on safe and effective values developed from data obtained from a sufficiently large representative population of patients for whom an SCDP device 200 of the type contemplated herein is appropriate.

In addition to an input device arrangement 226, the interface device 220 preferably includes an audio output device 228. Inputting of programmable parameters and confirmation of device programming is preferably communicated to the physician via the audio output device 228, which may employ relatively simple voice output electronics. Although the interface device 220 may incorporate a display device 224, it may be desirable to employ only a voice/audio user interfacing capability in order to minimize the complexity of the interface device 220.

The interface device 220 may include other features. The interface device 220 may include a communications interface 234 to facilitate communications between the interface device 220 and a network or personal computer 230 or other processing resource. For example, the interface device 220 may provide connectivity between the SCDP device 200 and an advanced patient management (APM) system via an appropriate network interface 234. An SCDP device 200 and interface device 220 (or other interfacing communications device) may be used within the structure of an APM system that allows physicians to remotely and automatically monitor cardiac functions, as well as other patient conditions if applicable. In one approach, an SCDP device 200 may be equipped with a communications device that enables real-time data collection, diagnosis, and treatment of the patient. Various embodiments described herein may be used in connection with advanced patient management. Methods, structures, and/or techniques described herein may be adapted to facilitate remote patient/device monitoring, diagnosis, and/or treatment, or other APM related methodologies. An SCDP device 200 of the present invention may incorporate device and/or system features disclosed in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In certain embodiments, the interface device 200 may include an interface for communicating with a personal computer 230 or other peripheral data processing system. The personal computer 230 may include software that facilitates the presentation of patient ECGs, SCDP device status, diagnostics, and event data, and other cardiac activity information for viewing by a physician. The personal computer 230 may include a network interface for communicating with another resource, such as an APM system. The interface device 220 or the personal computer 230 may include a data formatting module or software 232 that operates on raw data transferred from the SCDP device 200 to the interface device 220. Alternatively, the data formatting software 232 may be implemented within the interfacing device 200. The data formatting module 232 processes SCDP device data, such as ECGs with markers, in manner that is useful to the physician.

Figure 1C:
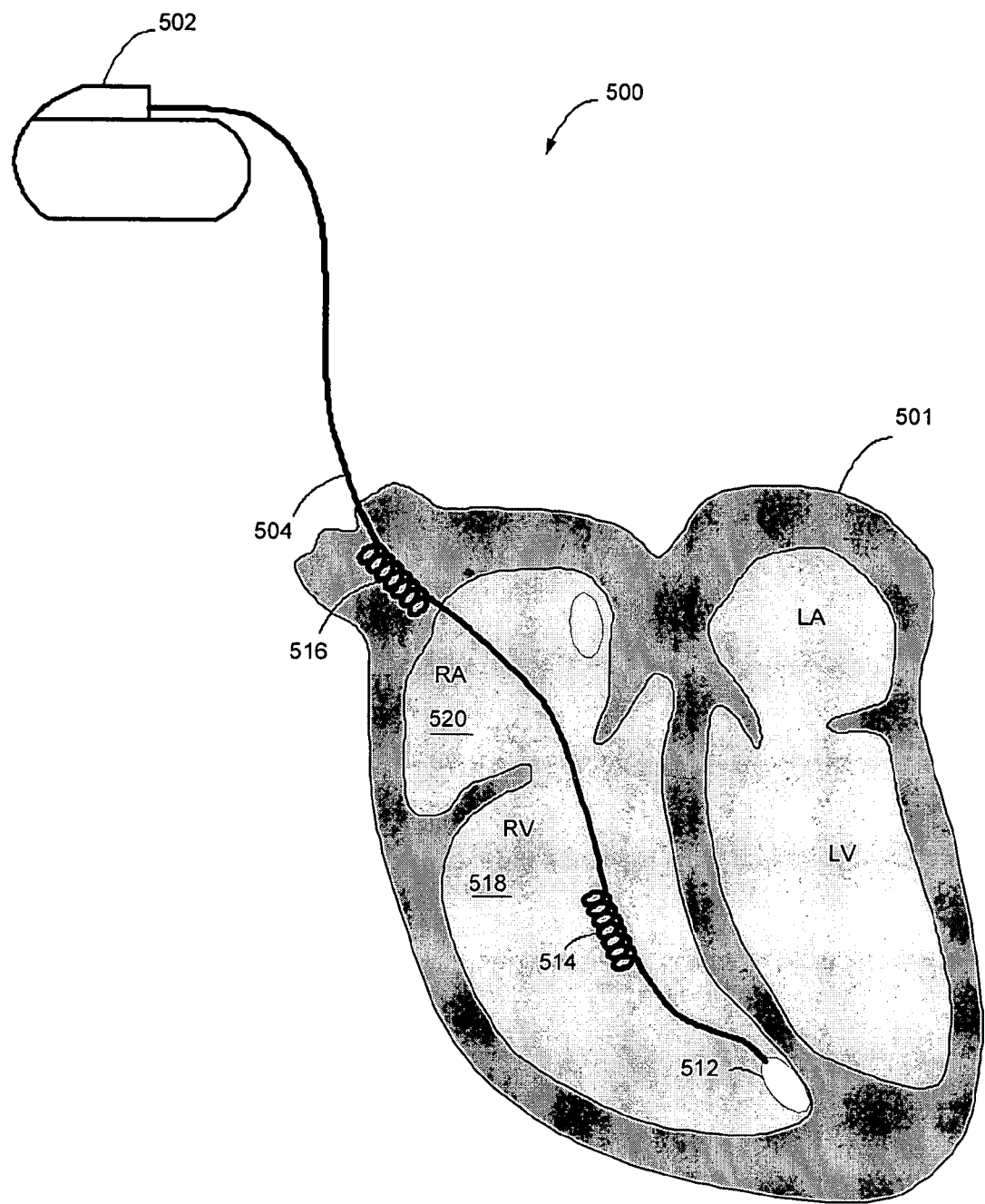
FIG. 1C is a depiction of an SCDP system implanted in a patient in accordance with an embodiment of the present invention.

FIG. 1C is a depiction of an SCDP system 500 implanted in a patient in accordance with an embodiment of the present invention. The SCDP system 500 includes an SCDP device 502 that is electrically and physically coupled to an intracardiac lead 504. The intracardiac lead 504 may be implanted in the body using various techniques, such as that previously described, with portions of the intracardiac lead 504 inserted into a heart 501. The intracardiac lead 504 is used to detect electric cardiac signals produced by the heart 501 and to provide electrical energy to the heart 501 under predetermined conditions to treat cardiac tachyarrhythmias and post-shock asystole of the heart 501. The SCDP device 502 is preferably not implemented to provide a conventional bradycardia pacing therapy, such as VVI pacing, or more complex pacing therapies, such as a resynchronization therapy.

The SCDP system 500 depicted in FIG. 1C is a single chamber device, capable of sensing signals produced by the right ventricle and providing cardioversion and/or defibrillation waveforms to the right ventricle 518 of the heart 501. Defibrillation waveforms, for example, may be monophasic, biphasic, or multiphasic (e.g., triphasic) waveforms of a known type. In an embodiment in which asystole prevention pacing is also made available, the SCDP device 502 produces pacing pulses in accordance with a non-physiologic, life sustaining pacing therapy, such as pacing therapy deliverable at a rate lower than a bradycardia pacing rate. In yet another embodiment in which anti-tachycardia pacing (ATP) is made available, the SCDP device 502 produces pacing pulses in accordance with an appropriate ATP therapy.

The intracardiac lead 504 shown in FIG. 1C includes an SVC-coil 516, an RV-coil 514, and an RV-tip electrode 512. The RV-coil 514, which can also serve as an RV-ring electrode, is spaced apart from the RV-tip electrode 512, which is a tip electrode. A can electrode may also be used in combination with, or as an alternate to, the SVC-coil electrode 516, for example. In the configuration of FIG. 1C, the intracardiac lead 504 is positioned within the heart 501, with a portion extending through the right atrium 520 into the right ventricle 518. The SVC-coil 516 is positioned at an appropriate location within the right atrium chamber 520 of the heart 501 or a major vein leading to the right atrium chamber 520 of the heart 501. The RV-coil 514 and SVC-coil 516 depicted in FIG. 1C are defibrillation coil electrodes.

It is believed that an SCDP device of the present invention may be used with cardiac lead configurations other than that shown in FIG. 1C. For example, a cardiac lead often referred to as a "VDD" lead may be employed. A VDD lead may be considered a variation on a conventional ventricular ICD lead in which an additional electrode or electrodes are integrated into the lead to sense atrial activity, but not to apply energy to the atria. Such a lead could be useful in preventing inappropriate therapies in an SCDP device.

By way of further example, it may be desirable to include a subcutaneous, non-intrathoracic electrode or electrode array configured for placement proximate the apex of the heart. A subcutaneous, non-intrathoracic electrode or electrode array may be used as a defibrillation electrode for purposes of delivering tachyarrhythmia therapy, and may also be used for cardiac activity sensing. One or more electrodes placed at a subcutaneous, non-intrathoracic location may enhance tachyarrhythmia detection, and far-field cardiac signals sensed at the subcutaneous, non-intrathoracic location may be used to verify or confirm presence or absence of a tachyarrhythmia event or episode. In a configuration that employs a subcutaneous, non-intrathoracic defibrillation electrode or electrode array, the SVC-coil 516 may not be required or desired.

Cardiac asystole may be sensed and/or confirmed using any of the available sense vectors associated with a given electrode arrangement. An asystole prevention pacing therapy may be delivered using an appropriate energy delivery vector, such as that associated with the tip electrode 512 and the RV-coil electrode 514 (operating as a bipolar electrode pair in this example).

Certain embodiments of the present invention illustrated herein are generally described as having various basic capabilities similar to those provided by a conventional implantable cardioverter/defibrillator. Exemplary ICD circuitry, structures and functionality, aspects of which can be incorporated in an SCDP device of the present invention, are disclosed in commonly owned U.S. Pat. Nos. 5,133,353; 5,179, 945; 5,314,459; 5,620,466; and 5,662,688, which are hereby incorporated herein by reference in their respective entireties. Certain embodiments of the present invention can implement functionality traditionally provided by cardiac monitors as are known in the art, in addition to providing cardioversion/defibrillation and asystole pacing therapies. Exemplary cardiac monitoring circuitry, structures and functionality, aspects of which can be incorporated in an SCDP device of the present invention, are disclosed in commonly owned U.S. Pat. Nos. 5,313,953; 5,388,578; and 5,411,031, which are hereby incorporated herein by reference in their respective entireties.

Figure 2:
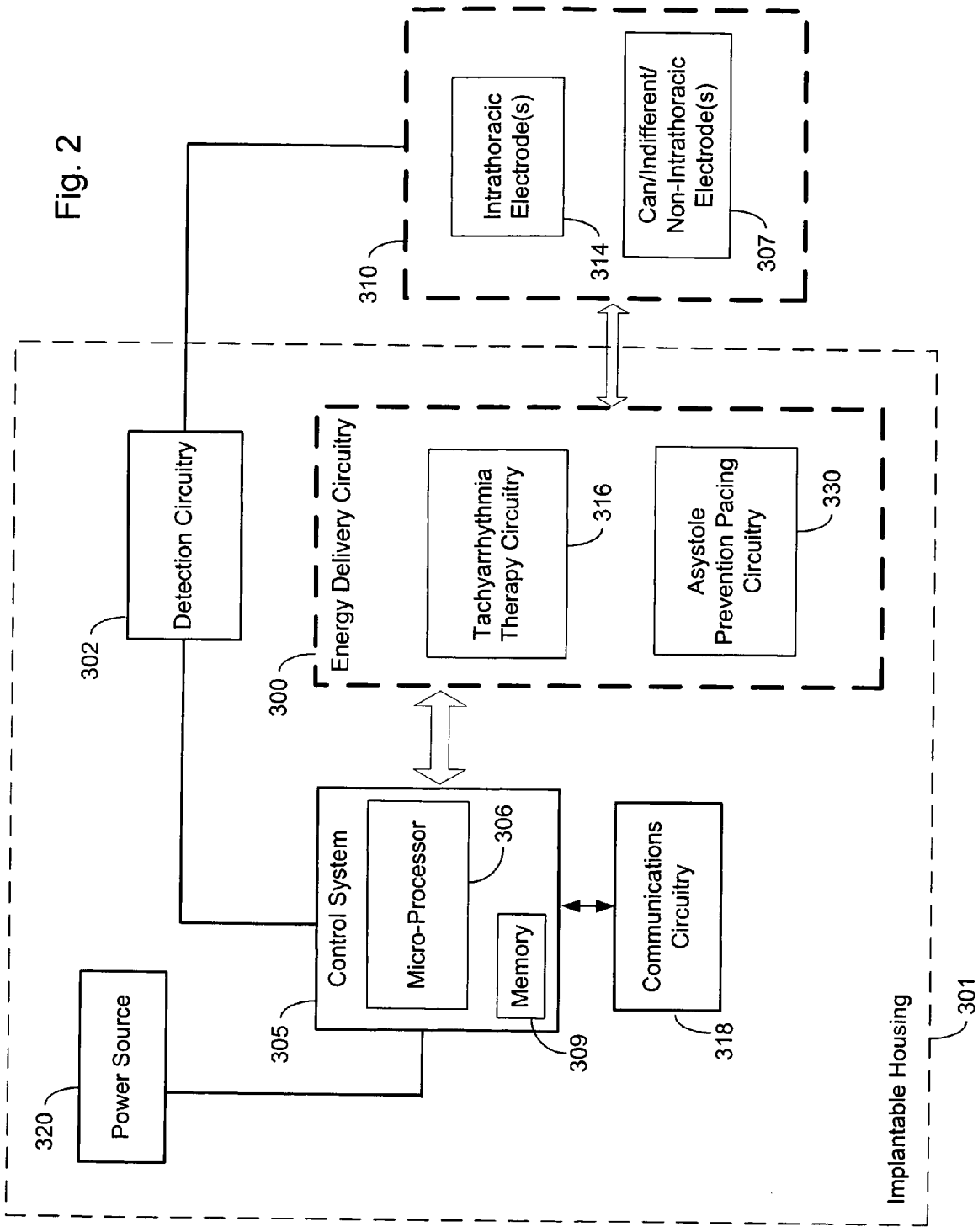
FIG. 2 is a block diagram showing various components of an SCDP device in accordance with an embodiment of the present invention.

FIG. 2 is a block diagram depicting various components of an SCDP device in accordance with an embodiment of the present invention. According to this embodiment, the SCDP device incorporates a processor-based control system 305 which includes a micro-processor 306 coupled to appropriate memory (volatile and non-volatile) 309, it being understood that any logic-based control architecture can be used. The control system 305 is coupled to circuitry and components to sense, detect, and analyze electrical signals produced by the heart and deliver electrical stimulation energy to the heart under predetermined conditions to treat cardiac tachyarrhythmias and asystole.

Cardiac signals are sensed using cardiac electrodes 310, which typically include one or more intrathoracic electrodes 314 (e.g., transvenous, endocardial or epicardial). The cardiac electrodes 310 may also include one or more subcutaneous, non-intrathoracic electrodes 307, such as a subcutaneous electrode array, or a can or indifferent electrode provide in or on the housing 301 of the SCDP device. As such, unipolar, bipolar, or combined unipolar/bipolar electrode configurations may be employed.

Sensed cardiac signals are received by detection circuitry 302, which includes sense amplification circuitry and may also include filtering circuitry. The detection circuitry 302 includes an analog-to-digital converter that converts the sensed cardiac signals from analog to digital form and communicates the signals to the control system 305. Memory circuitry 309 of the control system 305 is configured to store a reduced set of programmable parameters relative to those associated with conventional ICDs. For example, the memory circuitry 309 may be configured to facilitate storage and programmability of two SCDP device settings (e.g., rate threshold and sensing floor adjustment). The memory circuitry 309 is configured to store other parameters needed for operating the SCDP device. Further, the memory circuitry 309 can also be configured to store data indicative of cardiac signals received by the detection circuitry 302. For example, the memory circuitry 309 can be configured to store historical ECG and therapy related data, which may be used for various purposes and transmitted to an external receiving device as needed or desired.

The control system 305 of the SCDP device preferably performs automatic diagnostics that determine the status of the SCDP device. The automatic diagnostics provide an indication that a physician follow-up is required or desirable. For example, the control system 305 may determine the status of various key components to ensure safe operation of the SCDP device. The control system 305 preferably diagnoses SCDP device components and detects the following anomalous conditions: low battery, noise leading to diverted therapy, electrode fault, pulse generator fault, and events detected, and therapies delivered. This and other diagnostic data is preferably stored in the memory circuitry 309 for subsequent transfer to a patient-external communication device or system.

The control system 305 processes cardiac signal data received from the detection circuitry 302 and controls energy delivery circuitry 300 to initiate an appropriate tachyarrhythmia therapy to terminate cardiac arrhythmic episodes and return the heart to normal sinus rhythm. The control system 305 is coupled to tachyarrhythmia therapy circuitry 316. The tachyarrhythmia therapy circuitry 316 is coupled to the cardiac electrodes 310, which may include intrathoracic electrodes 314, non-intrathoracic electrodes 307, or selected ones or combinations of intrathoracic and non-intrathoracic electrode 314, 307.

Upon command, the tachyarrhythmia therapy circuitry 316 delivers cardioversion or defibrillation energy to the heart in accordance with a pre-established cardioversion or defibrillation therapy. In a less sophisticated embodiment, the tachyarrhythmia therapy circuitry 316 is controlled to deliver a defibrillation therapy, in contrast to an embodiment that provides for delivery of both cardioversion and defibrillation therapies. In a more sophisticated embodiment, the tachyarrhythmia therapy circuitry 316 may also be configured to deliver anti-tachycardia pacing (ATP) energy to the heart in accordance with a known ATP therapy.

For example, an ATP therapy (or a cardioversion therapy, such as a low voltage cardioversion therapy) may be delivered in a serial manner relative to defibrillation therapy delivery. In one approach, an ATP or cardioversion therapy may be delivered during or prior to charging the high voltage capacitor of the tachyarrhythmia therapy circuitry 316 for delivering defibrillation therapy. During the charging process and prior to delivering the defibrillation therapy, a check is made to determine if the arrhythmia has been terminated in response to the ATP or cardioversion therapy. If terminated, delivery of the defibrillation therapy is aborted or withheld, otherwise the defibrillation therapy is delivered. Exemplary ICD high energy delivery circuitry, structures and functionality, aspects of which can be incorporated in an SCDP device of the present invention, are disclosed in commonly owned U.S. Pat. Nos. 5,372,606; 5,411,525; 5,468,254; and 5,634,938, which are hereby incorporated herein by reference in their respective entireties.

An SCDP device of the present invention preferably incorporates a cardiac asystole prevention pacing capability in addition to cardioversion/defibrillation and/or anti-tachycardia pacing capabilities. As is shown in FIG. 2, the energy delivery circuitry 300 of an SCDP device can include asystole prevention pacing circuitry 330 which is coupled to the control system 305 and the cardiac electrodes 310. Upon command, the asystole prevention pacing circuitry 330 delivers pacing pulses to the heart in accordance with a pre-established asystole prevention pacing therapy, examples of which are discussed below.

An asystole prevention pacing therapy is typically delivered subsequent to delivery of defibrillation therapy, if needed, via the asystole prevention pacing circuitry 330 as shown in FIG. 2. Alternatively, and as discussed below, asystole prevention pacing therapies can be delivered via the tachyarrhythmia therapy circuitry 316, which effectively obviates the need for separate asystole prevention pacing circuitry 330.

Communications circuitry 318 is coupled to the microprocessor 306 of the control system 305. The communications circuitry 318 allows the SCDP device to communicate with a receiving device or system situated external to the patient. For example, the SCDP device can communicate with hand-held, portable interface device of the type described previously with regard to FIG. 1B. By way of further example, the SCDP device can communicate with a patient-worn or bed-side communication system via the communications circuitry 318. The communications circuitry 318 may also be configured to effect communications between the SCDP device and a programmer, network, personal computer, or other patient-external device.

Typically, the SCDP device is encased and hermetically sealed in a housing 301 suitable for implanting in a human body as is known in the art. Power to the SCDP device is supplied by an electrochemical power source 320 housed within the SCDP device.

Figure 3:
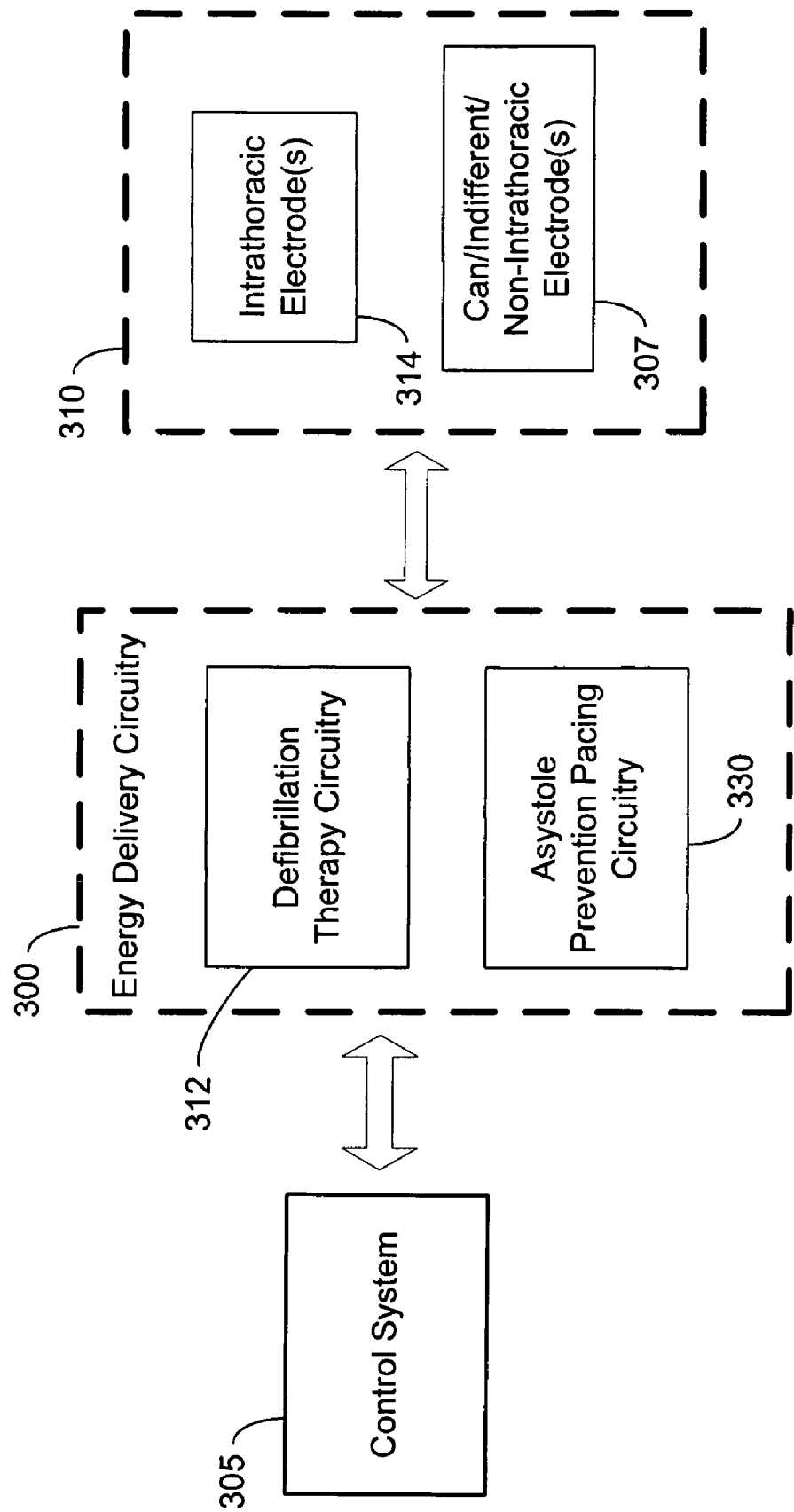
FIG. 3 is a block diagram illustrating energy delivery components of an SCDP device in accordance with an embodiment of the present invention.
Figure 4:
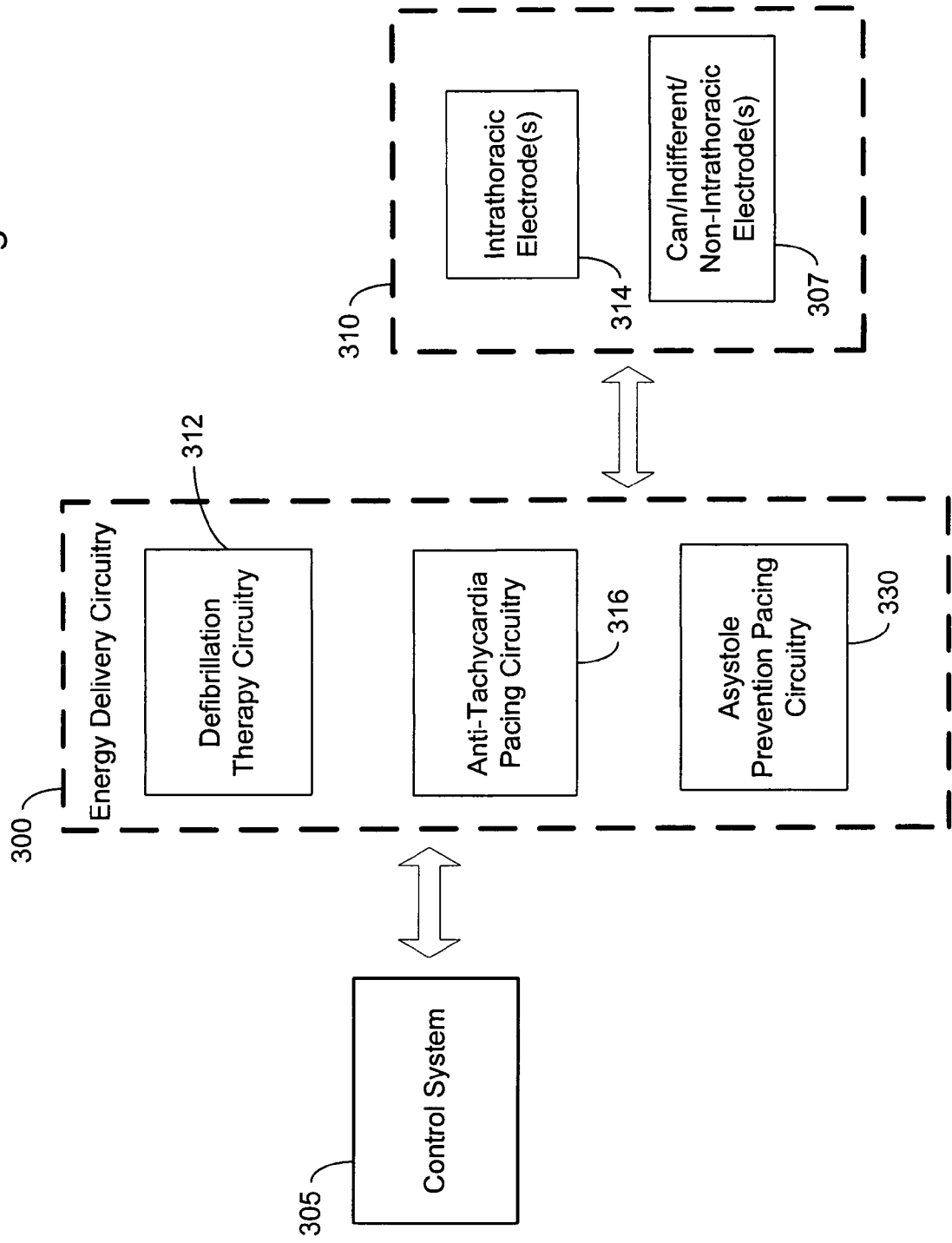
FIG. 4 is a block diagram illustrating energy delivery components of an SCDP device in accordance with another embodiment of the present invention.

FIGS. 3 and 4 illustrate two embodiments of energy delivery circuitry 300 that may be incorporated in an SCDP device of the present invention. In the embodiment shown in FIG. 3, the energy delivery circuitry 300 is shown to include defibrillation therapy circuitry 312 and asystole prevention pacing circuitry 330. The defibrillation and asystole prevention pacing circuitry 312, 330 may be of a conventional implementation or of a type described herein. According to the embodiment depicted in FIG. 3, the energy delivery circuitry 300 provides two forms of cardiac therapy—a tachyarrhythmia therapy (e.g., high-energy defibrillation therapy) and an asystole prevention pacing therapy.

FIG. 4 illustrates an embodiment of energy delivery circuitry 300 that includes anti-tachycardia pacing circuitry 316 in addition to defibrillation therapy circuitry 312 and asystole prevention pacing circuitry 330. The anti-tachycardia pacing circuitry 316 may be of a conventional implementation or of a type described herein. For example, anti-tachycardia pacing circuitry 316 and delivery may be implemented in a manner disclosed in commonly owned U.S. Pat. Nos. 6,400,986 and 6,292,696, which are hereby incorporated herein by reference in their respective entireties. According to the embodiment depicted in FIG. 4, the energy delivery circuitry 300 provides two forms of cardiac therapy—a tachyarrhythmia therapy (e.g., high-energy defibrillation therapy and/or anti-tachycardia pacing therapy) and an asystole prevention pacing therapy.

Figure 5:
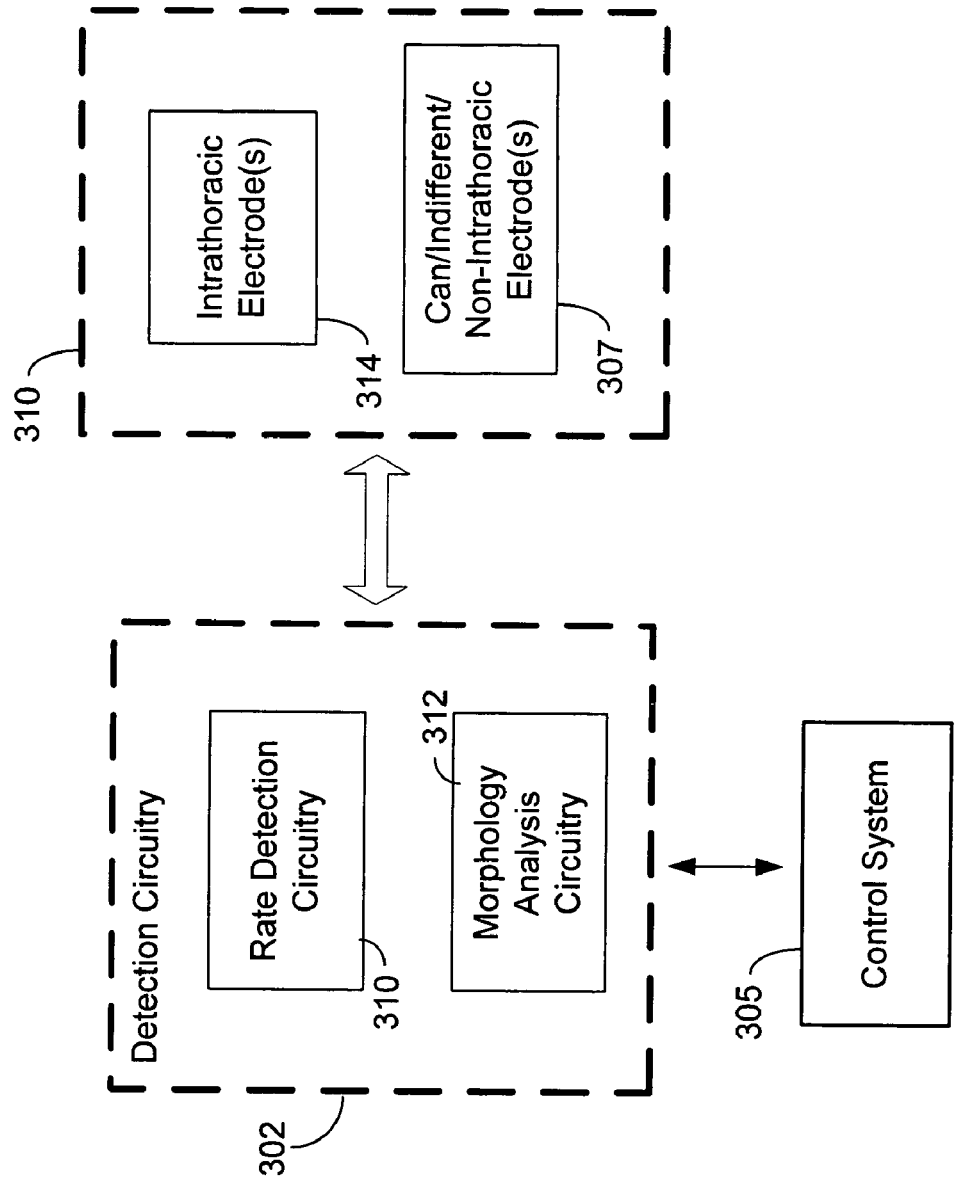
FIG. 5 is a block diagram illustrating detection circuitry components of an SCDP device in accordance with an embodiment of the present invention.

An embodiment of detection circuitry 302 is illustrated in FIG. 5. As discussed previously, the detection circuitry 302 includes sense amplification circuitry, optional filtering circuitry, and an analog-to-digital converter that converts the sensed cardiac signals from analog to digital form and communicates the signals to the control system 305. The detection circuitry 302 may further include a signal processor. The detection circuitry 302 coordinates analysis of sensed cardiac signals to detect cardiac tachyarrhythmias, including tachycardia and fibrillation (e.g., LTVAs). In one configuration, the detection circuitry 302 includes rate detection circuitry 310 that performs rate-based arrhythmia analysis on sensed cardiac signals in a manner known in the art.

In one approach, a single rate threshold may be established to indicate arrhythmic heart rates for which cardiac therapy is to be delivered. In another approach, two or more rate thresholds may be established to define rate zones, such as a tachycardia rate zone (VT) and a fibrillation rate zone (VF). According to this approach, an ATP therapy may be delivered for sustained arrhythmic heart rates falling into the tachycardia rate zone, and defibrillation therapy may be delivered for sustained arrhythmic heart rates falling into the defibrillation rate zone. Additional rate zones may be defined, such as a rate zone for which a low-energy cardioversion therapy may be appropriately delivered, in addition to at least a defibrillation rate zone.

Morphology analysis circuitry 312 may also be implemented in the detection circuitry 302, such as by the signal processor of the detection circuitry 302 executing morphological analysis algorithms. The morphology analysis circuitry 312 may be used to detect and verify the presence and severity of an arrhythmic episode. The morphology analysis circuitry 312 may also be used to determine the origin of a detected arrhythmia (e.g., atrial/SVT or ventricular origin via QRS complex width or other features). Tiered or parallel arrhythmia discrimination algorithms can also be implemented using both rate-based and morphologic-based approaches. Exemplary arrhythmia detection and discrimination circuitry, structures, and techniques, aspects of which can be implemented in an SCDP device of the present invention, are disclosed in commonly owned U.S. Pat. Nos. 5,301,677 and 6,438,410, which are hereby incorporated herein by reference in their respective entireties.

In accordance with an embodiment of the present invention, an SCDP device is configured to provide defibrillation and asystole prevention pacing therapies. According to another embodiment, an SCDP device is configured to provide defibrillation, asystole prevention pacing, and anti-tachycardia pacing therapies. In certain configurations, the SCDP device delivers pacing therapies using defibrillation therapy circuitry and one or more high voltage defibrillation capacitors, which eliminates the need for separate pacing therapy circuitry. In other configurations, pacing therapies of the present invention can be delivered by dedicated pacing therapy circuitry.

Embodiments of the present invention are directed to maintaining circulatory support by providing post-shock pacing pulses from an SCDP device. Embodiments of the present invention are directed to post-shock asystole prevention using post-shock pacing therapies. According to one approach, and in contrast to conventional bradycardia pacing modalities, normal heart rate is not maintained by the SCDP device. Rather, a single pacing pulse is delivered after a predetermined interval following detection of the last R-wave or delivery of a pace pulse (i.e., asystole detection). Delivery of post-shock pacing pulses is terminated once the heart is able to beat on its.

An SCDP device of the present invention can be programmed to detect cardiac asystole, such as may occur after delivery of a defibrillation therapy, and, in response, deliver a life sustaining, non-physiologic pacing therapy to terminate the detected cardiac asystole. The pacing therapy provides for delivery of pacing pulses at a rate substantially lower than a bradycardia pacing rate. The pacing therapy can involve delivery of pacing pulses at a progressively increasing rate, a progressively decreasing rate, or at a substantially constant rate over all or portion of the therapy duration. For example, a given pacing interval can be increased by a fixed amount or a certain percentage relative to a preceding pacing interval. The pacing therapy can alternatively involve delivery of a series of pacing pulses, where the series of pacing pulses includes at least one sequence delivered at a variable rate and at least one sequence delivered at a substantially constant rate. Once the patient's heart begins to pace on its own, post-shock pacing support is terminated for that episode.

Pacing, in this regard, is provided only as a means to maintain patient life post shock during asystole. A suitable pacing rate typically ranges between 2 and 40 pulses per minute (ppm), with 5-20 ppm representing a typical pacing rate. The pacing electrodes may be the same as the shock electrodes or can include one or more dedicated pacing electrodes.

In an embodiment of an SCDP device employing subcutaneous, non-intrathoracic electrodes, an asystole prevention pacing therapy may involve delivery of pacing pulses having pulse widths of between about 10 ms and about 30 ms. In an embodiment of an SCDP device employing intrathoracic electrodes, an asystole prevention pacing therapy may involve delivery of pacing pulses each having pulse widths of between about 0.06 ms and about 2 ms.

In one approach, energy to perform cardiac pacing support is provided by residual energy left on the defibrillation storage capacitor(s) subsequent to defibrillation therapy delivery. A maximum number of pacing pulses are deliverable post shock using the residual capacitor energy prior to charge depletion. This approach effectively eliminates the necessity of having a separate pacing circuit in the SCDP device. Instead, only a simple voltage or current regulator may be utilized to maintain the proper voltage levels. Pacing pulses are thus provided through the shock delivery circuit. In the event additional pacing is required, the energy storage capacitor can be quickly charged to a suitable level. It will be appreciated that this approach may be used for asystole prevention pacing and ATP, with appreciation of the maximum number of ATP pacing pulses deliverable prior to charge depletion. Additional details of this approach and other aspects of exemplary asystole prevention pacing structures and techniques are disclosed in commonly owned U.S. Pat. No. 7,392,081, which is hereby incorporated herein by reference.

Figure 6:
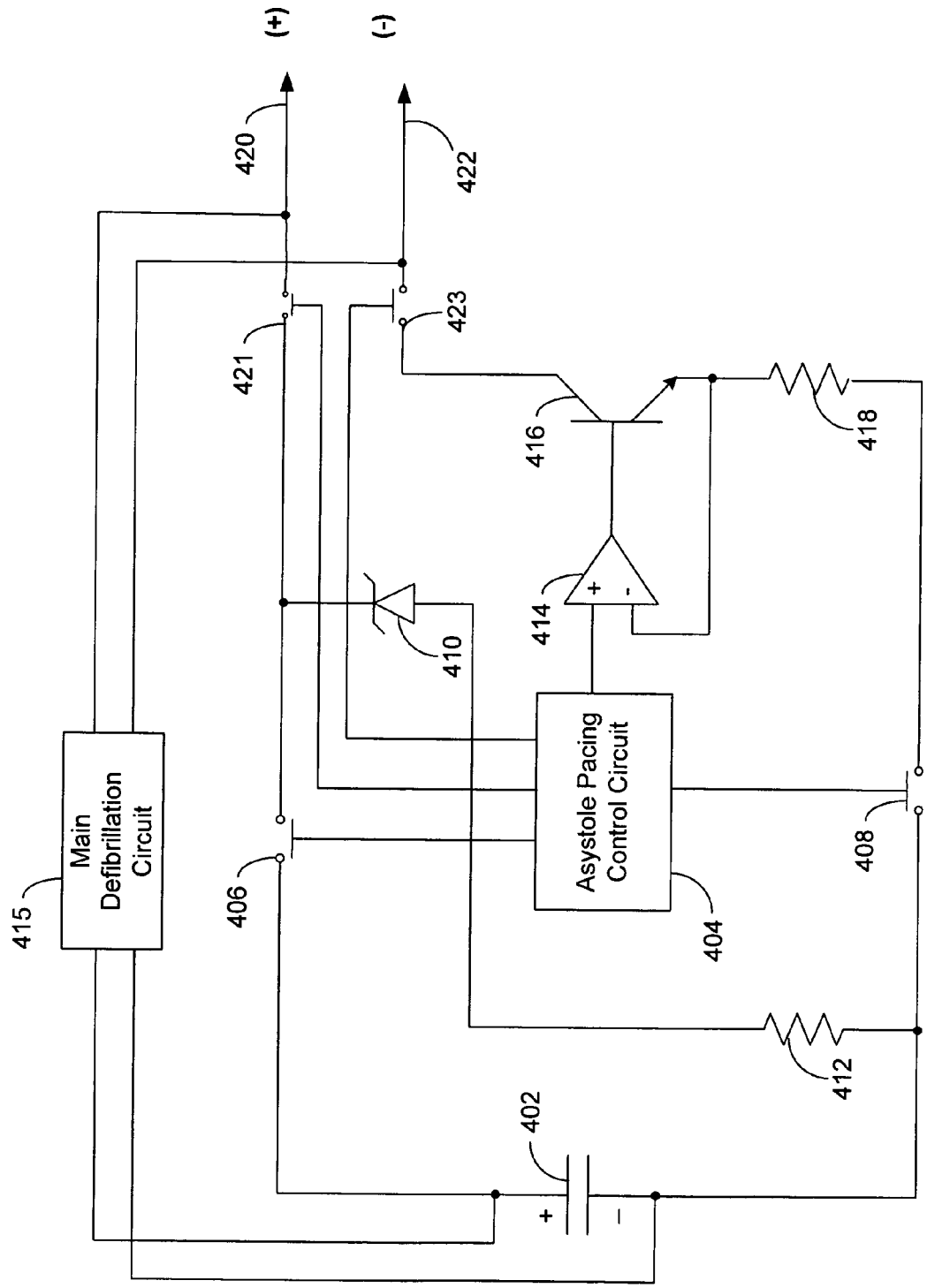
FIG. 6 is a schematic of circuitry for delivering a pacing therapy for terminating detected asystole in accordance with an embodiment of the present invention.

FIG. 6 is a simplified schematic of circuitry for delivering post-shock asystole prevention pacing in accordance with an embodiment of the present invention. The circuitry shown in FIG. 6 is coupled to, or otherwise incorporated within, the defibrillation circuit of the SCDP device, details of which are not shown for purposes of simplicity. The circuitry shown in FIG. 6 includes a defibrillation energy source 402, which is coupled to the main energy unit (e.g., battery, not shown) of the SCDP device. The defibrillation energy source 402 can include one or more high voltage capacitors of a type typically used in defibrillation devices.

The main defibrillation circuit 415 is shown coupled to high voltage terminals 420 and 422 and the defibrillation energy source 402. The pacing control circuit 404 is shown coupled to switches 406 and 408, which are respectively coupled to the defibrillation energy source 402 and high voltage terminals 420 and 422 via switches 421 and 423, respectively (switch 408 coupled to terminal 422 via pacing current control circuitry). Operation of the main defibrillation circuit 415 and pacing control circuit 404 is controlled by a control system (not shown) of the SCDP device to selectively enable and disable primary defibrillation circuitry, associated with shock therapy delivery, and asystole prevention circuitry, associated with pacing therapy delivery.

When in a defibrillation therapy delivery mode, switches 406, 408, 421 and 423 are opened, which disables the asystole prevention circuitry, enabling the main defibrillation circuitry 415 to delivery normal defibrillation therapy via terminals 420, 422 without interfering with the asystole prevention circuitry. When in a post-shock asystole prevention pacing mode, switches 406, 408, 421, and 423 are closed by the pacing control circuit 404, which enables the post-shock asystole prevention pacing circuitry. A desired pacing voltage is maintained across terminals 420, 422 via a Zener diode 410 (e.g., 200 V nominal or less) and a resistor 412. The pacing control circuit 404 can control the current of the pace pulses via transistor 416 and control amplifier 414.

It is noted that the main defibrillation circuitry 415 typically includes an H-bridge circuit (not shown) for switching the polarity of the defibrillation waveform during therapy delivery. Those skilled in the art will appreciate that other control circuit configurations can be implemented to provide post-shock asystole prevention pacing via a defibrillation energy source in accordance with the principles of the present invention.

Figure 7:
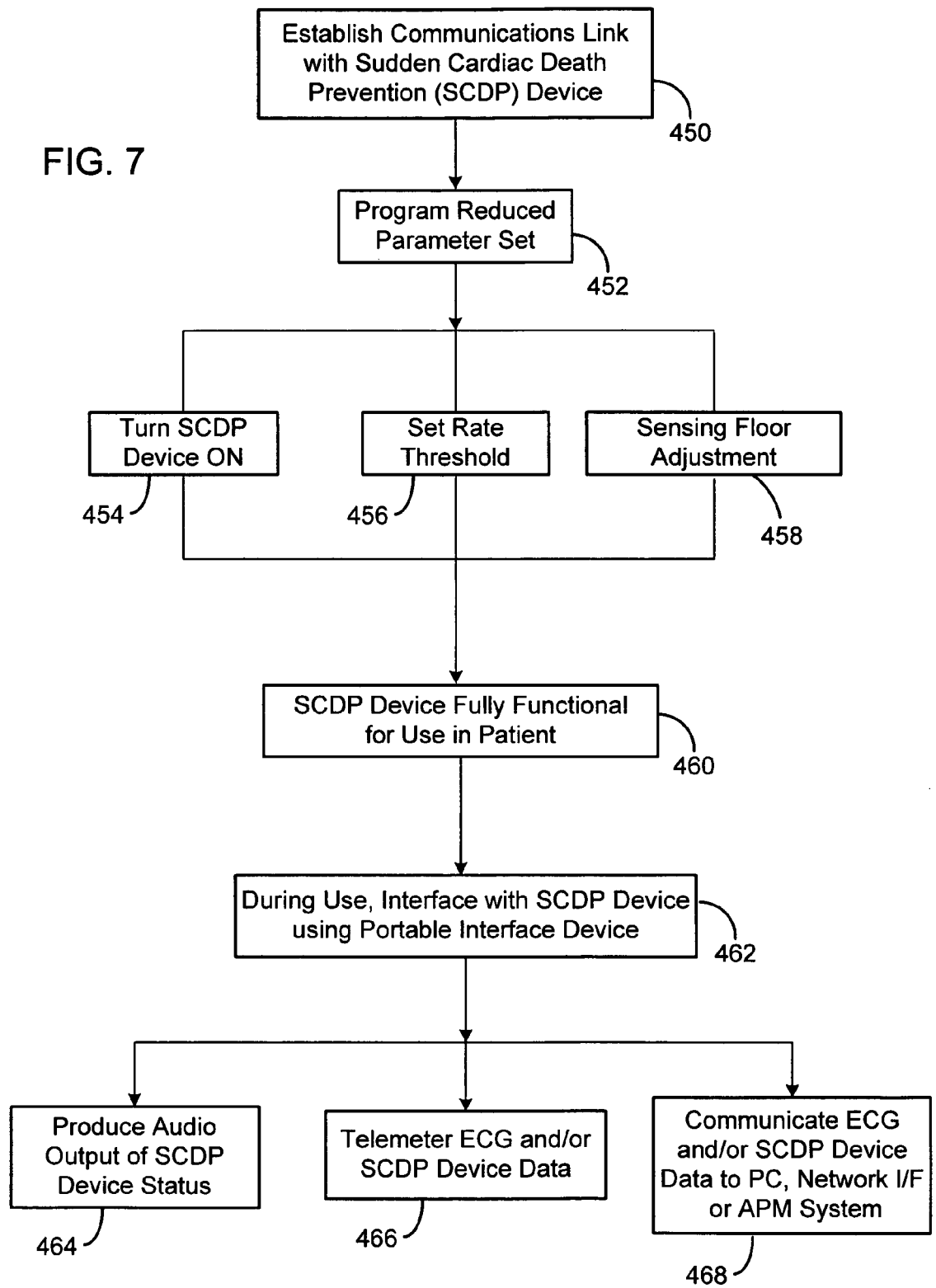
FIG. 7 is a flow diagram depicting various processes associated with programming and use of an SCDP device in accordance with an embodiment of the present invention.

FIGS. 7-12 are flow diagrams illustrating various processes associated with operation of an SCDP device in accordance with embodiments of the present invention. FIG. 7 is a flow diagram depicting various processes associated with programming and use of an SCDP device in accordance with an embodiment of the present invention. As is shown in FIG. 7, a communications link is established 450 between the SCDP device and a patient-external interface device, such as a hand-held of a type previously described. Each of a reduced set of programmable parameters is programmed 452 into the SCDP device. In the embodiment shown in FIG. 7, a rate threshold and a sensing floor adjustment are respectively set 456, 458. Therapy is enabled 454 by toggling a therapy On/Off parameter to the On state, at which point the SCDP device is fully functional for use 460 in a patient.

During operational use of the SCDP device, an interface device may be used to establish communication 462 with the SCDP device as needed or desired. The interface device may produce an audio output 464 concerning the status of the SCDP device, including the status of diagnostics, faults, and events. The SCDP device may telemeter 466 ECG and/or other SCDP device data to the interface device. The SCDP device may also, or alternatively, communicate 468 ECG and/or SCDP device data to a personal computer, network interface, or advanced patient management system, for example, via the interface device or other interfacing device.

Figure 8:
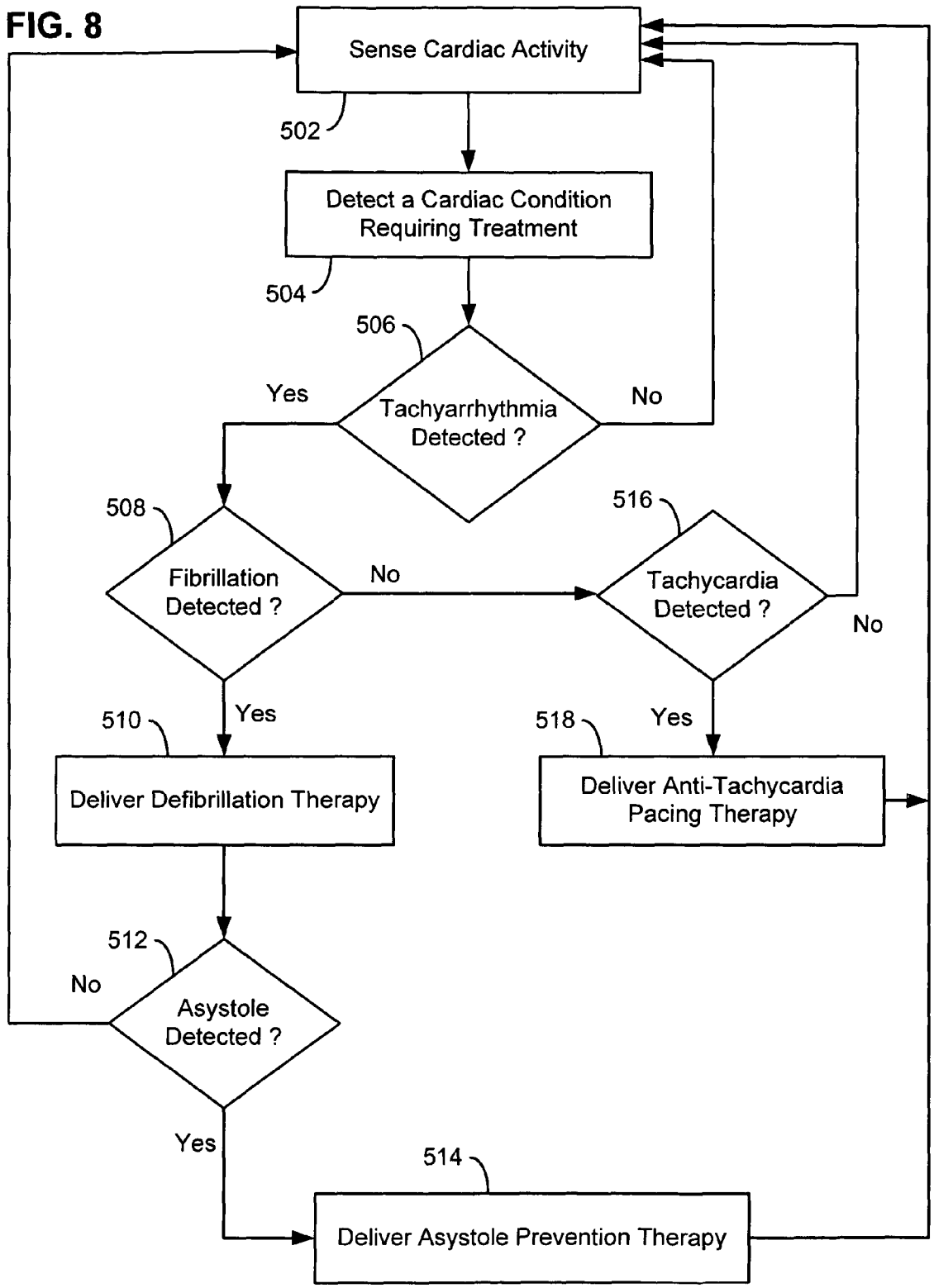
FIG. 8 illustrates various processes associated with cardiac therapy delivery in accordance with an embodiment of the present invention.

FIG. 8 illustrates various processes associated with cardiac therapy delivery in accordance with an embodiment of the present invention. According to the processes depicted in FIG. 8, cardiac activity is sensed 502 and a cardiac condition requiring treatment is detected 504. If a tachyarrhythmia is detected 506, it is determined whether the detected tachyarrhythmia is a tachycardia 516 or fibrillation 508. If ventricular fibrillation is detected 508, defibrillation therapy is delivered 510, although a cardioversion therapy may first be delivered followed by defibrillation therapy if unsuccessful. After successfully terminating the fibrillation event, a check is made 512 to determine if the patient's heart is in asystole. If so, asystole prevention pacing is delivered 514. Once the heart begins to beat on its own, the asystole prevention pacing therapy is terminated. If ventricular tachycardia is detected 516, anti-tachycardia pacing is delivered 518 in an attempt to return the heart to normal sinus rhythm. ATP therapy delivery 518 is preferably limited to a predetermined number of attempts.

Figure 9:
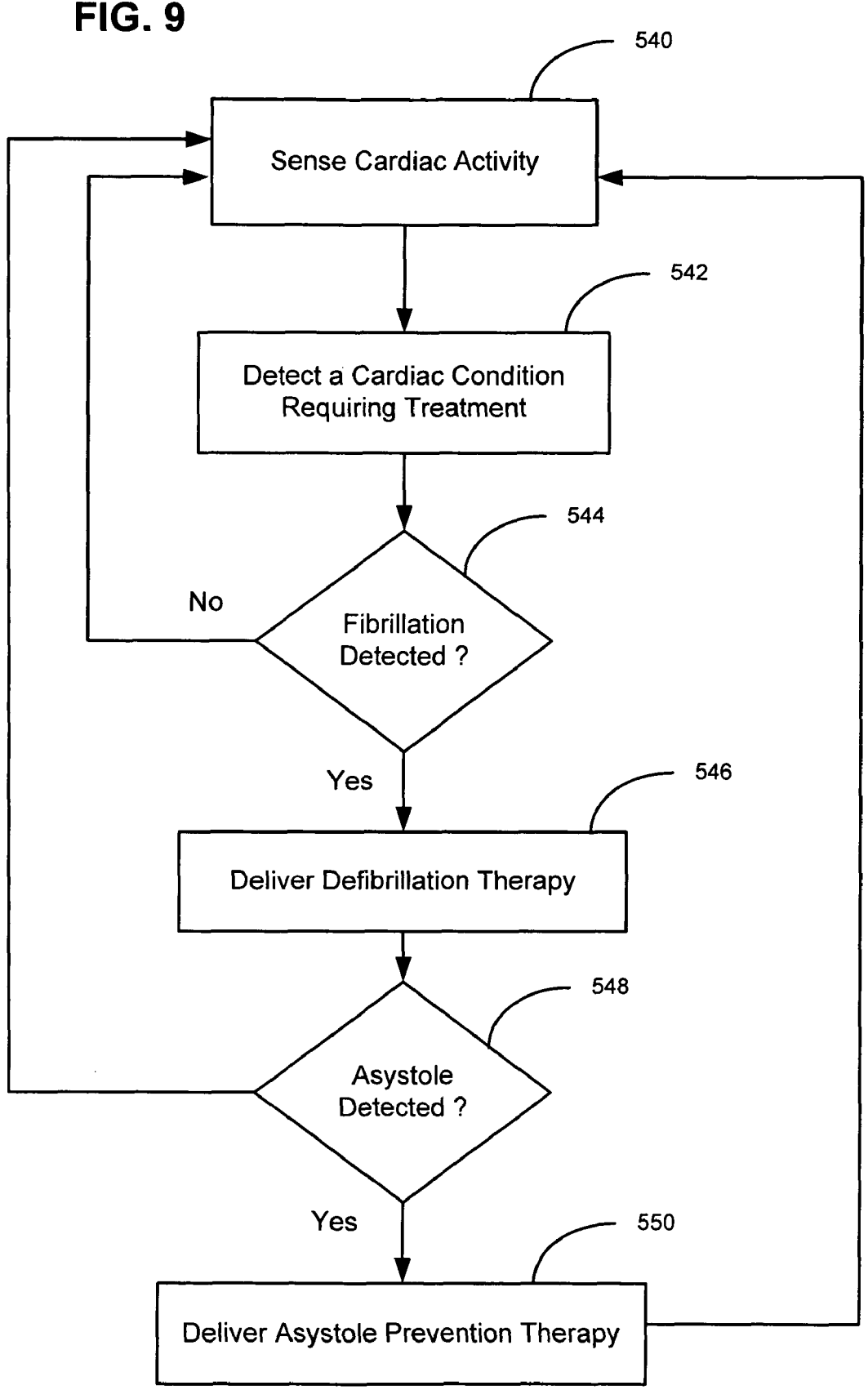
FIG. 9 illustrates various processes associated with cardiac therapy delivery in accordance with another embodiment of the present invention.

FIG. 9 illustrates various processes associated with cardiac therapy delivery in accordance with another embodiment of the present invention. According to the processes depicted in FIG. 9, the processes associated with ATP therapy in FIG. 8 (blocks 506, 516 and 518) are excluded. As shown in FIG. 9, cardiac activity is sensed 540 and a cardiac condition requiring treatment is detected 542. If ventricular fibrillation is detected 544, cardioversion and/or defibrillation therapy is delivered 546. After successfully terminating the fibrillation event, a check is made 548 to determine if the patient's heart is in asystole. If so, asystole prevention pacing is delivered 550 and subsequently terminated upon the heart beginning to beat on its own.

Figure 10:
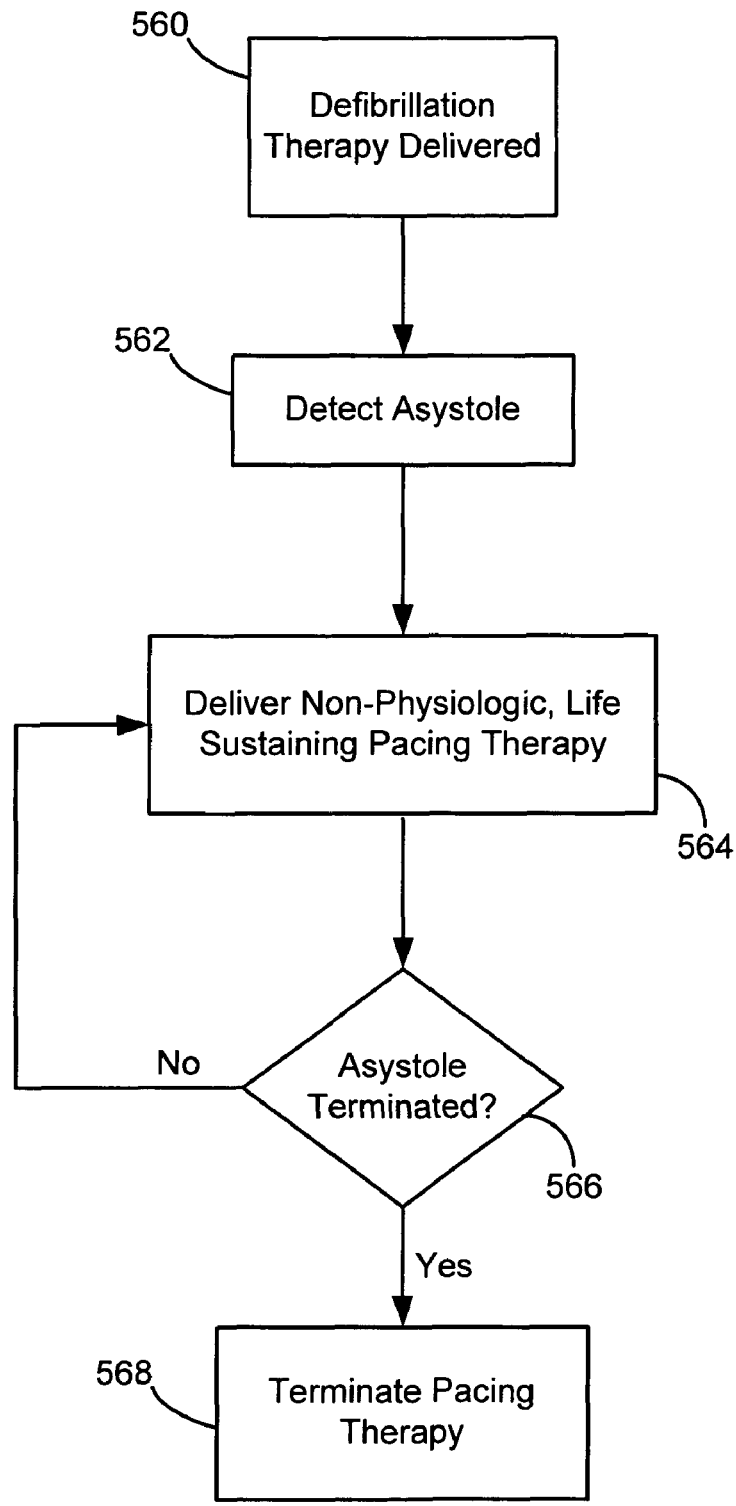
FIG. 10 is a flow diagram showing various processes associated with a pacing therapy for terminating detected asystole in accordance with an embodiment of the present invention.

FIG. 10 is a flow diagram showing additional processes associated with a pacing therapy for terminating detected asystole following defibrillation therapy delivery in accordance with an embodiment of the present invention. According to this embodiment, defibrillation therapy is delivered 560 in response to the SCDP device detecting and confirming a ventricular fibrillation episode. Upon detecting 562 post-shock asystole of the heart, the SCDP device delivers a non-physiologic, life sustaining transthoracic pacing therapy 564 in an attempt to terminate asystole. If the SCDP device determines 566 that asystole has not abated, the SCDP device continues to deliver non-physiologic, life sustaining transthoracic pacing therapy 564. The pacing therapy is terminated 568 in response to the SCDP device detecting successful termination of asystole.

Figure 11:
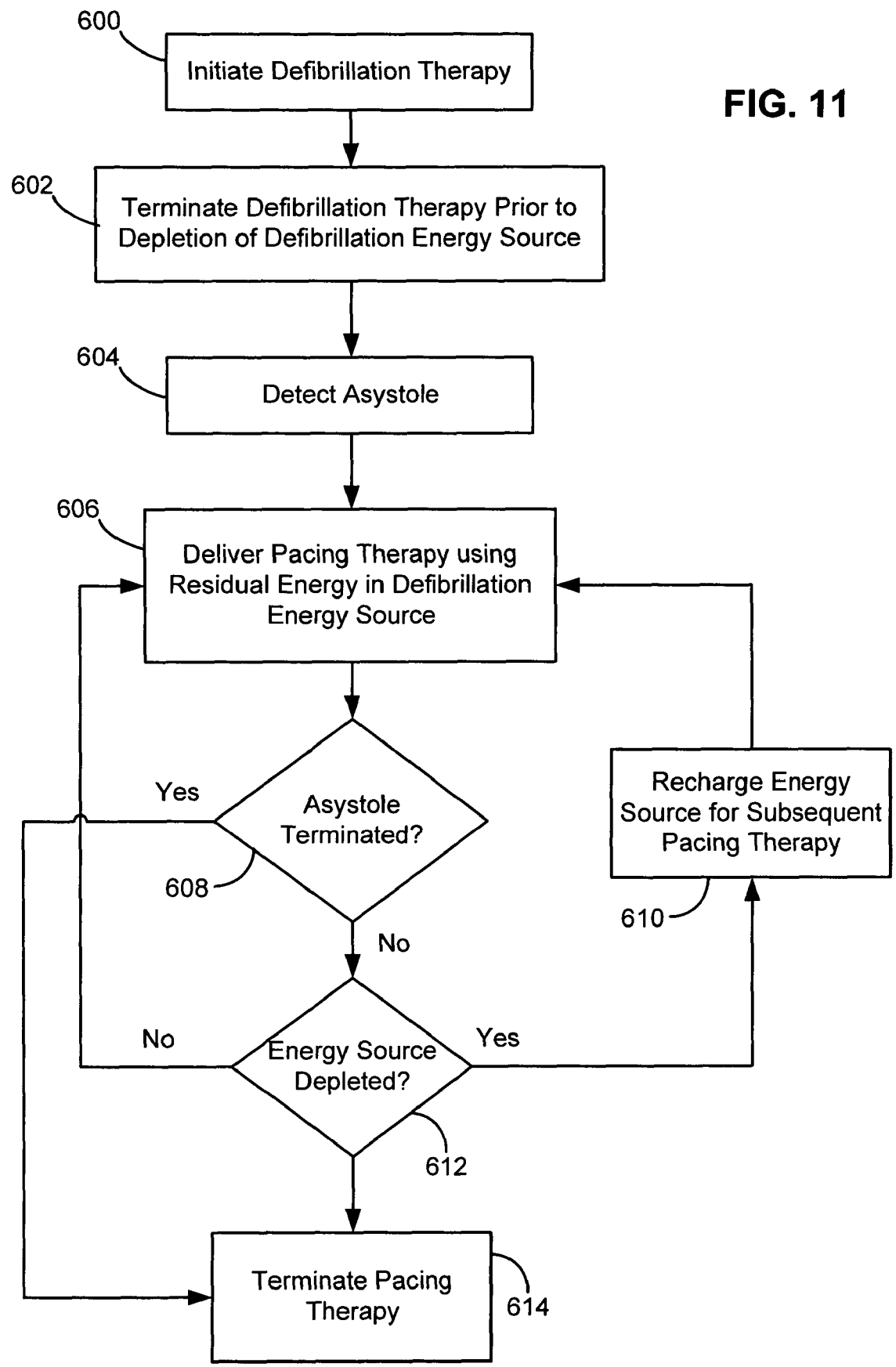
FIG. 11 is a flow diagram illustrating various processes associated with a pacing therapy for terminating detected asystole, wherein energy for the pacing therapy is provided by a defibrillation energy storage source in accordance with an embodiment of the present invention.

FIG. 11 is a flow diagram showing various processes associated with a pacing therapy for terminating detected asystole following defibrillation therapy delivery in accordance with another embodiment of the present invention. According to this embodiment, defibrillation therapy is initiated 600 in response to the SCDP device detecting and confirming a ventricular fibrillation episode as previously described. Defibrillation therapy is terminated 602 prior to depletion of the defibrillation energy source.

The defibrillation waveform is selected to provide delivery of defibrillation energy sufficient to terminate ventricular fibrillation, while leaving sufficient energy to subsequently deliver one or more pacing pulses prior to depleting the high voltage defibrillation capacitor(s). For example, the defibrillation therapy can reduce a voltage of the defibrillation energy storage source from a first voltage level to a second voltage level, and the pacing therapy can be delivered at voltage levels equal to or less than the second voltage level. The first and second voltage levels are selected primarily to provide effective defibrillation therapy and then secondarily to provide adequate residual strength for a duration of post-shock asystole prevention pacing therapy.

Upon detecting 604 post-shock asystole, the SCDP device delivers a pacing therapy 606 using energy remaining in the defibrillation energy source in an attempt to terminate asystole. If asystole is successfully terminated 608, then transthoracic pacing therapy is terminated 614. If asystole is not terminated 608, then a check 612 is made to determine if sufficient energy remains in the defibrillation energy source to support delivery of a pacing therapy. If depleted and asystole persists, the defibrillation energy source is recharged 610 to a depth of charge sufficient to support redelivery of the previously selected pacing therapy or another pacing therapy directed to terminating asystole. The recharging process can be repeated after delivery of a single pace pulse or a series of pulses, assuming an R-wave is not detected after delivery of a given pulse, thus indicating persistence of asystole. Depending on the duration of asystole persistence, the depth of charge can be varied from one recharge cycle to another to meet the pacing energy demands associated with a given pacing therapy. The pacing therapy is terminated 614 in response to the SCDP device detecting successful termination of asystole.

Figure 12:
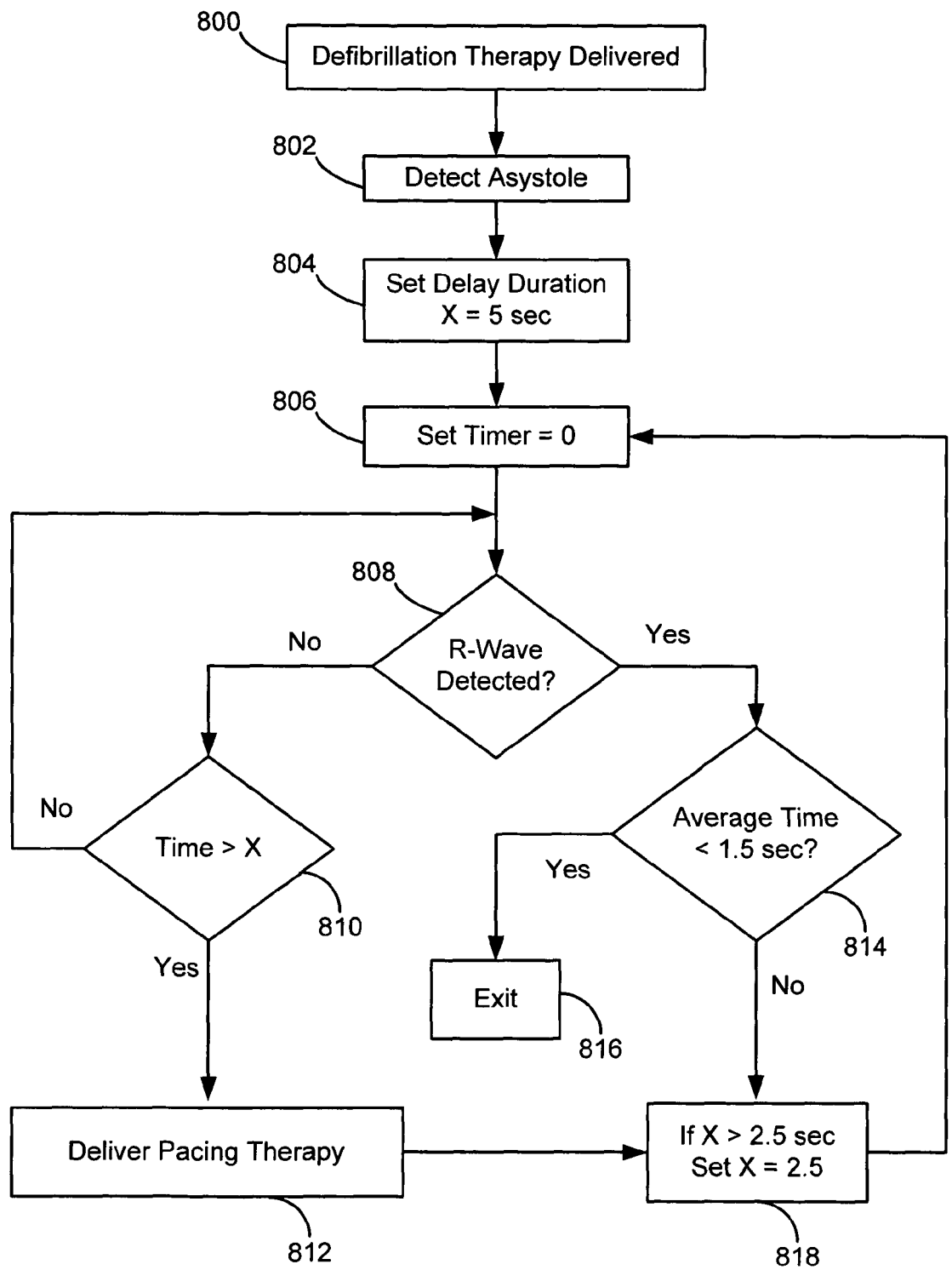
FIG. 12 is a flow diagram illustrating various processes associated with a pacing therapy for terminating detected asystole in accordance with another embodiment of the present invention.

An embodiment of a pacing methodology employing post-shock asystole prevention timing is depicted in FIG. 12. According to this embodiment, defibrillation therapy is delivered 800 in response to the SCDP device detecting and confirming a ventricular fibrillation episode as previously discussed. Upon detecting 802 post-shock asystole, a control system of the SCDP device initiates post-shock asystole prevention timing which controls the delivery of a pacing therapy in a manner depicted in FIG. 12. It is understood that cardiac sensing is continuous during the processes depicted in FIG. 12.

A delay duration, X, is set 804, such as X=5 seconds. The delay duration is representative of the amount of time that post-shock asystole prevention pacing is delayed after detection of asystole. This delay period is selected to allow for the spontaneous termination of asystole for a particular patient or patient population, which would obviate the need for post-shock asystole prevention pacing. In the illustrative embodiment of FIG. 12, the delay duration, X, is set to 5 seconds, it being understood that the delay duration, X, can range from about 2-3 seconds up to about 30 seconds.

A timer is initialized 806 by setting the timer to 0. The SCDP device senses for cardiac activity, in the form of R-wave detection. If an R-wave is detected 808, and the average time between 2 or more successive detected R-waves is determined 814 to be less than 1.5 seconds, then the SCDP device confirms that asystole has been terminated and the pacing therapy routine is exited 816. If the average time between detected R-waves is not less than 1.5 seconds 814, then the delay duration, X, is set to X=2.5 seconds if X is greater than 2.5 seconds 818, otherwise the current value of the delay duration, X, is retained. The timer is reinitialized to 0, and processing continues at process 806.

If an R-wave is not detected 808 and the timer has exceeded 810 the delay duration, X, then pacing therapy is delivered 812. The delay duration, X, is set to X=2.5 seconds if X is greater than 2.5 seconds 818, otherwise the current value of the delay duration, X, is retained. This reduction in the delay duration, X, effectively shortens the time to the next pacing pulse, assuming an R-wave is not detected. Although process 818 can initially reduce the delay duration, X, by 50%, it is understood that the delay duration, X, can be shortened by greater or less than 50%, such as between 30% and 80% of a preceding delay duration. Moreover, the delay duration, X, can be progressively reduced until a predetermined minimum duration is reached, such as by reducing the delay duration, X, by a fixed percentage or fixed amount of time until the predetermined minimum duration is reached.

Figure 13:
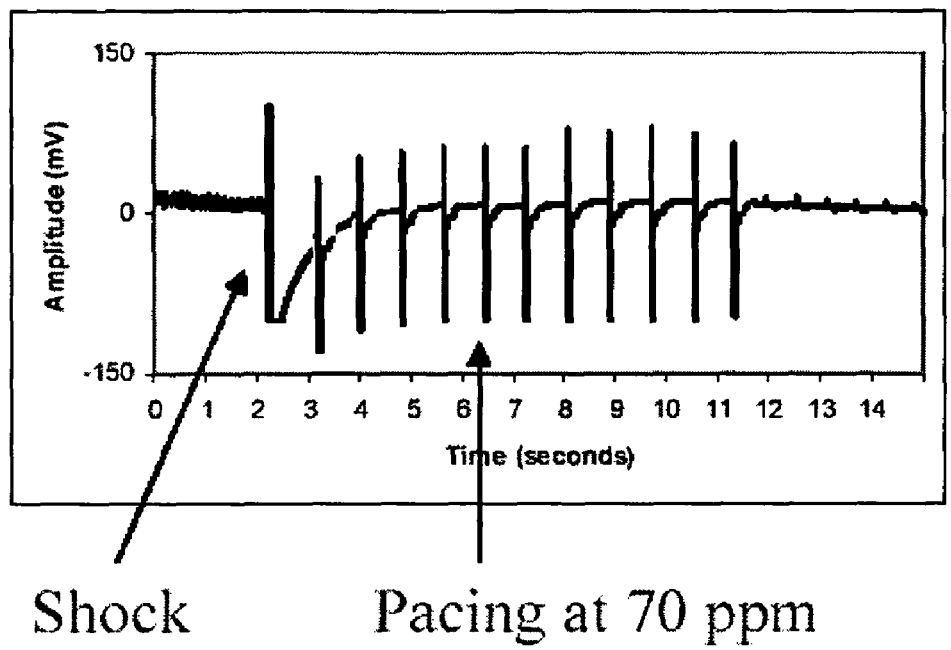
FIG. 13 is an illustration of a typical bradycardia pacing waveform sequence associated with a conventional post-shock pacing mode.

FIG. 13 is a waveform sequence illustrating typical bradycardia pacing (e.g., VVI) subsequent to defibrillation therapy. Post-shock pacing according to a conventional approach involves pacing the heart at a physiologic rate, such as at 70 ppm. The waveform shown in FIG. 14, in contrast to that of FIG. 13, illustrates post-shock asystole prevention pacing according to an embodiment of the present invention. One skilled in the art will readily appreciate that the pacing waveform shown in FIG. 14 represents a non-physiologic pacing therapy that delivers pacing pulses at a rate substantially below a conventional bradycardia pacing rate, but at a rate sufficient to sustain life.

Figure 14:
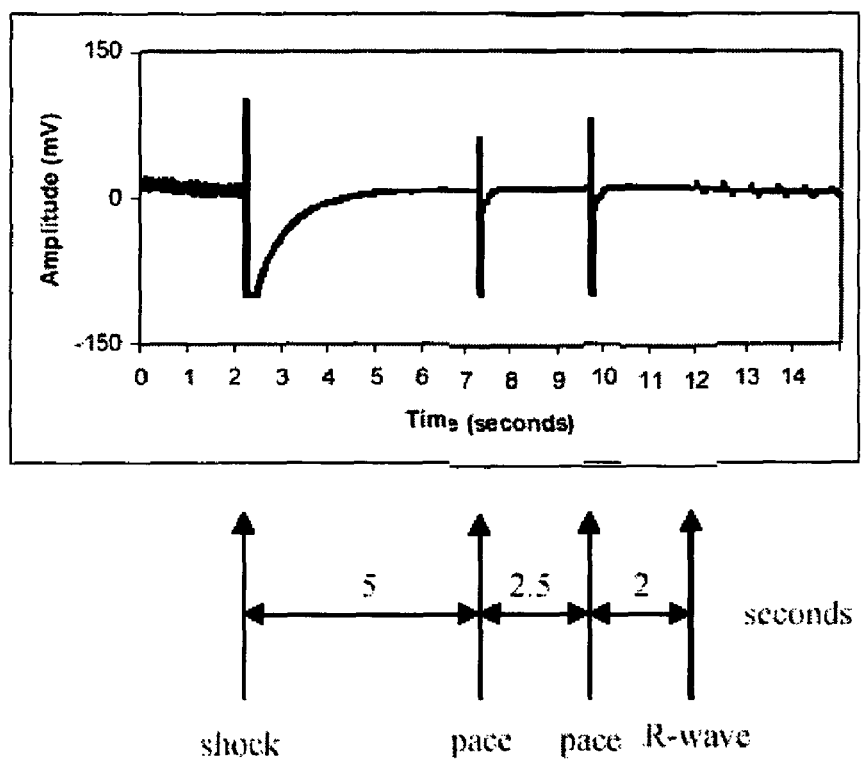
FIG. 14 is a waveform sequence representative of a pacing therapy for terminating detected asystole in accordance with an embodiment of the present invention.

FIG. 14 further illustrates one approach to post-shock asystole prevention pacing in which the pacing rate progressively increases to a predetermined maximum pacing rate at predetermined increments. By way of example, and as is shown in FIG. 14, the first pace pulse following detection of post-shock asystole is delayed by a predetermined initial delay period, such as 5 seconds. Upon detecting non-termination of asystole after delivering the first pace pulse, a second delay period (e.g., 2.5 seconds) is initiated which is shorter in duration than the initial delay period. A second pace pulse is delivered after expiration of the second delay period.

Upon detecting non-termination of asystole after delivering the second pace pulse, a third delay period (e.g., 2.0 seconds) is initiated which is shorter in duration than the second delay period. If necessary, another pace pulse would be delivered after expiration of the third delay period. This progression in pacing interval decrease continues until a predetermined minimum pacing interval (maximum pacing rate) is reached, such as a pacing interval of 2.0 seconds. In the illustrative example shown in FIG. 14, an R-wave is detected prior to the end of the third delay period, thereby inhibiting the third pace pulse. Subsequent R-waves occur at an average interval that exceeds the minimum pacing interval, and pacing is terminated.

It will be appreciated that other pacing therapies can be implemented in accordance with a post-shock asystole prevention pacing methodology of the present invention. For example, pacing pulses can be delivered at a rate varying between about 2 and about 40 pulses per minute. According to one approach, a first pace pulse can be delivered after an initial delay of about 5 to 30 seconds subsequent to detection of the cardiac asystole, and subsequent pace pulses can be delivered at an increased pacing rate, such as at a progressively increasing or decreasing rate.

For example, a first pace pulse can be delivered after a first duration subsequent to detection of the cardiac asystole, and a second pace pulse can be delivered after a second duration subsequent to the first pace pulse, where the second duration can range between about one-third and about three-fourths of the first duration. A series of pacing pulses can alternatively be delivered at a substantially constant rate. A post-shock asystole prevention pacing therapy can also involve delivering a series of pacing pulses, where the series of pacing pulses includes at least one sequence delivered at a variable rate and at least one sequence delivered at a substantially constant rate.

Figure 15:
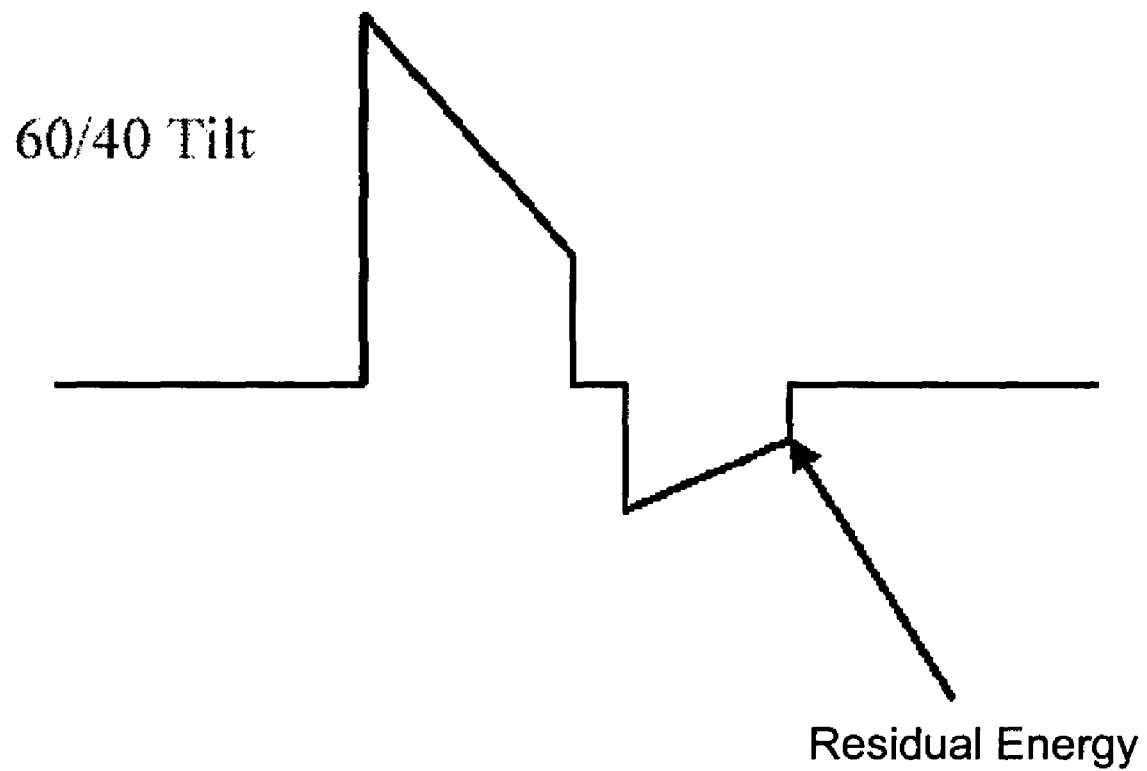
FIG. 15 is a defibrillation waveform that provides for residual energy sufficient to support a pacing therapy for terminating detected asystole in accordance with an embodiment of the present invention.

FIG. 15 illustrates a defibrillation waveform of a type suitable for implementing a post-shock asystole prevention pacing therapy in accordance with an embodiment of the present invention. In general, the defibrillation waveform is selected to provide delivery of defibrillation energy sufficient to terminate ventricular fibrillation, while leaving sufficient energy to subsequently deliver at least one, and more preferably a series of, pacing pulses prior to depleting the remaining defibrillation energy in the storage source. In particular, the overall tilt of the shock waveform can be selected to provide for a residual charge on the defibrillation capacitor(s) sufficient to deliver one or a series of pacing pulses prior to capacitor depletion.

The shock waveform shown in FIG. 15, for example, has a so-called 60/40 tilt, which results in an overall tilt of 76% given the characteristics of the particular capacitor (e.g., 150 µF capacitor) of the defibrillation circuitry. In general, an overall tilt of 70%-80% is typically sufficient to provide enough residual energy to support post-shock asystole prevention pacing therapy. In other words, the residual energy to be used for post-shock asystole prevention pacing therapy is typically 10% or less of the total energy of the capacitor(s) when fully charged for defibrillation therapy. However, the overall tilt of the defibrillation waveform can range between about 0% and 90%. It is noted that the defibrillation waveform can be a monophasic, a biphasic, or a multiphasic (e.g., triphasic) waveform of a known type. For example, the defibrillation waveform can be a biphasic, truncated exponential waveform.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable device for preventing sudden cardiac death, comprising:
    a housing configured for implantation in a patient;
    energy delivery circuitry provided in the housing, the energy delivery circuitry configured to deliver only two forms of cardiac therapy, the two forms of cardiac therapy comprising a non-physiologic, life sustaining pacing therapy and a therapy to treat a tachyarrhythmia;
    detection circuitry provided in the housing, the detection circuitry configured to detect cardiac rhythms;
    a lead system comprising one or more lead electrodes, the lead system coupled to the energy delivery circuitry and the detection circuitry; and
    control circuitry provided in the housing and coupled to the energy delivery circuitry and the detection circuitry, the control circuitry configured to coordinate delivery of the tachyarrhythmia therapy in response to the detection of a tachyarrhythmia requiring treatment and delivery of the non-physiologic, life sustaining pacing therapy in response to detection of cardiac asystole,
    wherein the non-physiologic, life sustaining pacing therapy comprises delivery of pacing pulses at a rate between 5-20 pulses per minute.

2. The device of claim 1, wherein the tachyarrhythmia therapy comprises a single therapy to treat cardiac fibrillation.

3. The device of claim 1, wherein the pacing therapy comprises a single pacing therapy to treat the cardiac asystole.

4. The device of claim 1, wherein the tachyarrhythmia therapy comprises a single therapy to treat cardiac fibrillation, and the pacing therapy comprises a single pacing therapy to treat the cardiac asystole.

5. The device of claim 1, wherein the pacing therapy comprises a single pacing therapy to treat the cardiac asystole, and the tachyarrhythmia therapy comprises a first therapy to treat cardiac fibrillation and a second therapy to treat a tachycardia.

6. The device of claim 1, wherein the tachyarrhythmia therapy comprises a therapy to treat a tachycardia.

7. The device of claim 1, wherein the tachyarrhythmia therapy comprises an anti-tachycardia pacing therapy.

8. The device of claim 1, wherein the tachyarrhythmia therapy comprises a therapy to treat cardiac fibrillation.

9. The device of claim 1, wherein the tachyarrhythmia therapy comprises a monophasic defibrillation therapy.

10. The device of claim 1, wherein the tachyarrhythmia therapy comprises a biphasic defibrillation therapy.

11. The device of claim 1, wherein the tachyarrhythmia therapy comprises a therapy to treat tachycardia and a therapy to treat cardiac fibrillation.

12. The device of claim 1, wherein the energy delivery circuitry comprises a capacitor circuit and the tachyarrhythmia therapy comprises a defibrillation therapy and a cardioversion therapy, the cardioversion therapy delivered prior to or during charging of a capacitor of the capacitor circuit.

13. The device of claim 1, wherein at least some of the lead electrodes are configured for intrathoracic placement.

14. The device of claim 1, wherein one or more of the lead electrodes are configured for subcutaneous non-intrathoracic placement.

15. The device of claim 1, wherein the housing comprises a housing electrode.

16. The device of claim 1, wherein the control circuitry coordinates delivery of pacing pulses having pulse widths of between about 10 ms and about 30 ms.

17. The device of claim 1, wherein the control circuitry coordinates delivery of pacing pulses each having pulse widths of between about 0.06 ms and about 2 ms.

18. The device of claim 1, wherein the control circuitry coordinates delivery of pacing pulses at a progressively increasing rate over a predetermined duration of time.

19. The device of claim 1, wherein the control circuitry coordinates delivery of pacing pulses at a progressively decreasing rate over a predetermined duration of time.

20. The device of claim 1, wherein the control circuitry coordinates delivery of pacing pulses at a substantially constant rate over a predetermined duration of time.

* * * * *